United States Patent [19]
Albertsen et al.

[11] Patent Number: 5,478,369
[45] Date of Patent: Dec. 26, 1995

[54] NUCLEOTIDE SEQUENCES MEDIATING MALE FERTILITY AND METHOD OF USING SAME

[75] Inventors: Marc C. Albertsen, West Des Moines; Larry R. Beach, Des Moines; John Howard, Des Moines; Gary A. Huffman, Des Moines, all of Iowa

[73] Assignee: Pioneer Hi-Bred International, Inc., Des Moines, Iowa

[21] Appl. No.: 103,739

[22] Filed: Aug. 2, 1993

Related U.S. Application Data

[63] Continuation-in-part of Ser. No. 537,183, Jun. 12, 1990, abandoned.
[51] Int. Cl.⁶ .............................. A01H 1/00; C12N 15/11; C12N 15/82
[52] U.S. Cl. ................ 47/58; 47/DIG. 1; 435/172.3; 536/23.1; 536/23.6
[58] Field of Search .......................... 435/172.3, 172.1; 47/58.03, 58.05; 536/23.1, 23.6

[56] References Cited

U.S. PATENT DOCUMENTS

| | | | |
|---|---|---|---|
| 5,190,931 | 3/1993 | Inouye | 435/91 |
| 5,208,149 | 5/1993 | Inouye | 435/91 |

FOREIGN PATENT DOCUMENTS

| | | |
|---|---|---|
| 4945690 | 8/1990 | Australia . |
| 329308 | 8/1989 | European Pat. Off. . |
| 0465024 | 1/1992 | European Pat. Off. . |
| 8910396 | 11/1989 | WIPO . |
| 9109957 | 7/1991 | WIPO . |
| 9218625 | 10/1992 | WIPO . |

OTHER PUBLICATIONS

Mariani, Celestina, et al., "Induction of male sterility in plants by a chimaeric ribonuclease gene", *Nature*, vol. 347, Oct. 25, 1990, pp. 737–741.
Benfy, Philip N., et al., "Regulated Genes in Transgenic Plants", *Science*, vol. 244, issued Apr. 14, 1989, pp. 174–181.
Forkmann, G., et al., "Selection and characterization of flavanone 3-hydroxylase mutants of Dahlia, Streptocarpus, Verbena and Zinnia", *Planta*, (1984), 161:261–265.
Balcells, L., et al., "Transposons as Tools for the Isolation of Plant Genes", *Tibtech*, vol. 9, Jan., 1991.
Chandlee, J., "The Utility of Transposable Elements as Tools for the Isolation of Plant Genes", *Physiologia Plantarum*, 79:105–115, Copenhagen, 1990.
Chandler, V., et al., "The *Mu* Elements of *Zea mays*", *Advances in Genetics*, see preprint to appear at vol. 30, pp. 1–73, 1992.
Hanson, D., et al., "Characterization of a Pollen–Specific cDNA Clone from *Zea mays* and Its Expression", *The Plant Cell*, vol. 1, 173–179, Feb., 1989.
Herdenberger, F., et al., "Isolation of Flower–Specific cDNA Clones from Sunflower", *Plant Science*, 669:111–122, 1990.
Izawa, T., et al., "Introduction and Transposition of Maize Transposable Element Ac in Rice", *Mol. Gen. Genet.*, vol. 227, No. 3, 1991. Abstract Only.
Mascarenhas, J., "The Isolation and Expression of Pollen–Expressed Genes", *Current Science*, vol. 58, No. 18, Sep. 20, 1989, pp. 1008–1015.

(List continued on next page.)

Primary Examiner—Gary Benzion
Attorney, Agent, or Firm—Pioneer Hi-Bred International, Inc.

[57] ABSTRACT

Nucleotide sequences mediating male fertility in plants are described, with DNA molecule and amino acid sequences set forth. Use of the nucleotide sequences to mediate fertility in plants is also described. In one such method, an inducible promoter is used to regulate expression of the DNA molecule. The control sequences are modified so that it is normally "off" and as a result the plants are male sterile. When it is desired to reproduce the male sterile plants, male fertility is restored by treating the plants with a non-phytotoxic chemical which induces expression of the critical gene.

18 Claims, 8 Drawing Sheets

OTHER PUBLICATIONS

Pear, J. et al., "Isolation and Characterization of a Fruit-Specific cDNA and the Corresponding Genomic Clone from Tomato", *Plant Molecular Biology*, 13:639–651, 1989.

Peterhans, A., et al., "Intrachromosomal Recombination in Plants", *The EMBO Journal*, vol. 9, No. 11, pp. 3437–3445, 1990.

Raghavan, V., "mRNAs and A Cloned Histone Gene Are Differentially Expressed During Anther and Pollen Development in Rice", *Journal of Cell Science*, 92:217–229, 1989.

Reddy, A. S. M., et al., "Molecular Cloning of cDNAs for Auxin-Induced mRNAs and Developmental Expression of the Auxin-Inducible Genes", *Plant Molecular Biology*, 14:643–653, 1990.

Rommens, C., et al., "A Transposon Tagging Strategy With Ac on Plant Cell Level and Heterologous Plant Species", *Plant Science*, 74:99–106, 1991.

Schweinfest, C., et al., "Subtraction Hybridization cDNA Libraries From Colon Carcinoma and Hepatic Cancer", *Genet. Annal. Tech. Appl.*, 7:64–70, 1990.

Smith, A., et al., "Identification and Characterization of Stamen-and Tapetum Specific Genes from Tomato", *Mol. Gen. Genet.*, 222:9–16, 1990.

Sommer, H., et al., "Deficiens, A Homeotic Gene Involved in the Control of Lower Morphogenesis in *Antirrhinum majus*: The Protein Shows Homology to Transcription Factors", *EMBO Journal*, vol. 9, No. 3, pp. 605–613, 1990.

Sotelo, J., et al., "Cloning, Sequence Analysis, and Expression of a cDNA Encoding a Plastid Localized Heat Shock Protein in Maize", *Plant Physiol.*, 93:1321–1328, 1990.

Twell, D., et al., "Isolation and Expression of an Anther-Specific Gene from Tomato", *Mol. Gen. Genet.*, 217:240–245, 1989.

Weiland, I., et al., "A Method for Difference Cloning: Gene Amplification Following Subtractive Hybridization", *Proc. Nat'l Acad. Sci. USA*, vol. 87, pp. 2720–2724, Apr., 1990.

Yoder, J. I., et al., "Progress Towards Gene Targeting in Plants", *Genetic Engineering*, vol. 13 (Plenum Press, New York, 1991).

Frova, C., et al., "Isozyme and HSP Gene Expression During Male Gametophyte Development in Maize", *Isozymes: Current Topics in Biological and Medical Research*, vol. 15, Genetics, Development, and Evolution 97–120 (1987).

Ryder, T., et al., "Elicitor rapidly induces chalcone synthase mRNA in *Phaseolus vulgaris* cells at the onset of the phytoalexin defense response", *Proc. Nat'l Acad. Sci. USA*, vol. 81 (1984) pp. 5724–5728.

Koller, B., et al., "Inactivating the $\beta_2$ microglobulin locus in mouse embryonic stem cells by homologuous recombination", *Proc. Nat'l Acad. Sci. USA* vol. 86 (1989) pp. 8932–8935.

Coe, Edward H., et al., "White pollen in maize", *The Journal of Heredity*, 72:318–320 (1981).

Albertsen, Marc, et al., "Developmental Cytology of 13 Genetic Male Sterile Loci in Maize", *Can. J. Genet. Cytol.*, 23:195–208, 1981.

Doring, H. P., "Tagging Genes with Maize Transposable Elements. An Overview", *Maydica* 34 (1989): 73–88.

Klein, T. M., et al., "Factors Influencing Gene Delivery into Zea may Cells by High-Velocity Microprojectiles", *Biotechnology*, vol. 6, May 1988, pp. 559–563.

Klein, T. M., et al., "Genetic Transformation of Maize Cells by Particle Bombardment", *Plant Physiol*, (1989) 91, 440–444.

Lyznik, L., et al., "Stable Co-Transformation of Maize Protoplasts with *gus* A and *neo* Genes", *Plant Molecular Biology*, 13:151–161 (1989).

Rhodes, C., et al., "Genetically Tranformed Maize Plants from Protoplasts", *Science*, vol. 240, 240–207 (8 Apr. 1988).

Wiegand, R., et al., "Messenger RNA Encoding a Glutathione-S-Transferase Responsible for Herbicide Tolerance in Maize is Induced in Response to Safener Treatment", *Plant Molecular Biology*, 7:235–243 (1986).

Moffat, Anne Simon, "Excess Genetic Baggage Dumped", *Science*, vol. 254, No. 5037, p. 1457 (1991).

Paszkowski, Jerzy, et al., "Gene Targeting in Plants", *The EMBO Journal*, vol. 7, No. 13, pp. 4021–4026 (1988).

Lechelt, Christa, et al., "Isolation and molecular analysis of the maize P locus", *Mol. Gen. Genet.* (1989) 219:225–234.

Chen, Jychian, et al., "Transposition of Ac From the P Locus of Maize into Unreplicated Chromosomal Sites", *Genetics*, 117:109–116 (Sep., 1987).

Chen, Jychian, et al., "Molecular Analysis of Ac Transposition and DNA Replication", *Genetics*, 130:665–676 (Mar., 1992).

Stadler, L. J., "On the Genetic Nature of Induced Mutations in Plants", reprinted from the Proceedings of the Sixth International Congress of Genetics, vol. 1, pp. 274–294, 1932.

Neuffer, M. G., et al., "Paraffin Oil Technique for Treating Mature Corn Pollen with Chemical Mutagens", *Maydica* XXIII (1978):21–28.

Rao, B. Subra, "A Case of Genic Male Sterility Induced by Sodium Azide in Pearl Millet", *Biol. Zentralbl*, 104 (1985) 519–521.

Conger, B. V., et al., "Mutagenic Effectiveness and Efficiency of Sodium Azide Versus Ethyl Methanesulfonate in Maize: Induction of Somatic Mutations at the $yg_2$ Locus by Treatment of Seeds Differing in Metabolic State and Cell Population", *Mutation Research*, 46 (1977) 285–296.

Filippetti, A., et al., "Improvement of Seed Yield in Vicia Faba L. By Using Experimental Mutagenesis II Comparison of Gamma-Radiation and Ethyl-Methane-Sulphonate (EMS) in Production of Morphological Mutants", *Euphytica* 35 (1986) 49–59.

Thurling, N., et al., "EMS Induction of Early Flowering Mutatnts in Spring Rape (*Brassica napus*)", *Plant Breeding* 108, 177–184 (1992).

Foulkes, Nicholas, et al., "More is Better: Activators and Repressors from the Same Gene", *Cell*, vol. 68, 411–414, Feb. 7, 1992.

Scheid, Ortrun M., et al., "Reversible inactivation of a transgene in *Arabidopsis thaliana*", *Mol. Gen. Genet.* (1991) 228:104–112.

Brusslan, Judy A., et al., "An Arabidopsis Mutatnt with a Reduced Level of cab140 RNA Is a Result of Cosuppression", *the Plant Cell*, vol. 5, 667–677, Jun. 1993.

Holzmayer, Tatyana A., et al., "Isolation of dominant negative mutants and inhibitory antisense RNA sequences by expression selection of random DNA fragments", *Nucleic Acids Research*, vol. 20, No. 4, 711–717.

Helene, Claude, et al., "Specific regulation of gene expression by antisense, sense and antigene nucleic acids", *Biochimica at Biophysica Acta*, 1049 (1990) 99–125.

Bourque, June E., et al., "Suppression of gene expression in plant cells utilizaing antisense sequences transcribed by RNA polymerase III", *Plant Molecular Biology*,

19:641–647, 1992.

Aarts, Mark G. M., "Transposon tagging of a male sterility gene in *Arabidopsis*", *Nature*, vol. 363, 24 Jun. 1993, pp. 715–717.

van der Krol et al. (1988) Anti-sense chalcone synthase gene in transgenic plants inhibits flower pigmentation. Nature, vol. 333, pp. 866–869.

```
              A  L  A  L  A  L  L  V  A  V  A  D  P  F  G  L
HN92 742 #2   GCCCTGGCCCTGGCCCTCCTAGTCGCGGTCGCGACCCGTTCGGCCTC
              ||||||||||||||||||||||    |||||||||||||||||||||||
MS45          GCCCTGGCCCTGGCCCTCCTA     GTCGCGACCCGTTCGGCCTC
              A  L  A  L  A  L  L        V  A  D  P  F  G  L
```

FIG. 7

NUCLEOTIDE SEQUENCES MEDIATING MALE FERTILITY AND METHOD OF USING SAME

REFERENCE TO PRIOR APPLICATION

This application is a continuation-in-part of previously filed and U.S. application Ser. No. 537,183, filed Jun. 12, 1990, now abandoned.

BACKGROUND OF THE INVENTION

The goal of plant breeding is to combine in a single variety/hybrid various desirable traits of the parental lines. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size, is important.

Field crops are bred through techniques that take advantage of the plant's method of pollination. A plant is self-pollinating if pollen from one flower is transferred to the same or another flower of the same plant. A plant is cross-pollinated if the pollen comes from a flower on a different plant.

In Brassica, the plant is normally self sterile and can only be cross-pollinated. In self-pollinating species, such as soybeans and cotton, the male and female plants are anatomically juxtaposed. During natural pollination, the male reproductive organs of a given flower pollinate the female reproductive organs of the same flower.

Maize plants (*Zea mays* L.) present a unique situation in that they can be bred by both self-pollination and cross-pollination techniques. Maize has male flowers, located on the tassel, and female flowers, located on the ear, on the same plant. It can self or cross pollinate. Natural pollination occurs in maize when wind blows pollen from the tassels to the silks that protrude from the tops of the incipient ears.

A reliable method of controlling male fertility in plants would offer the opportunity for improved plant breeding. This is especially true for development of maize hybrids, which relies upon some sort of male sterility system.

The development of maize hybrids requires the development of homozygous inbred lines, the crossing of these lines, and the evaluation of the crosses. Pedigree breeding and recurrent selection are two of the breeding methods used to develop inbred lines from populations. Breeding programs combine desirable traits from two or more inbred lines or various broad-based sources into breeding pools from which new inbred lines are developed by selfing and selection of desired phenotypes. A hybrid maize variety is the cross of two such inbred lines, each of which may have one or more desirable characteristics lacked by the other or which complement the other. The new inbreds are crossed with other inbred lines and the hybrids from these crosses are evaluated to determine which have commercial potential. The hybrid progeny of the first generation is designated $F_1$. In the development of hybrids only the $F_1$ hybrid plants are sought. The $F_1$ hybrid is more vigorous than its inbred parents. This hybrid vigor, or heterosis, can be manifested in many ways, including increased vegetative growth and increased yield.

Hybrid maize seed is typically produced by a male sterility system incorporating manual detasseling. Alternate strips of two inbred varieties of maize are planted in a field, and the pollen-bearing tassels are removed from one of the inbreds (female). Providing that there is sufficient isolation from sources of foreign maize pollen, the ears of the detasseled inbred will be fertilized only with pollen from the other inbred (male), and the resulting seed is therefore hybrid and will form hybrid plants. Unfortunately, the manual detasseling process is not entirely reliable. Occasionally a female plant will be blown over by a storm and escape detasseling. The natural variation in plant development can also result in plants tasseling after manual detassling is completed. Or, a detasseler will not completely remove the tassel of the plant. In either event, the female plant will successfully shed pollen and some female plants will be self-pollinated. This will result in seed of the female inbred being harvested along with the hybrid seed which is normally produced.

Alternatively, the female inbred can be mechanically detasseled. Mechanical detasseling is approximately as reliable as manual detasseling, but is faster and less costly. However, most detasseling machines produce more damage to the plants than manual detasseling. Thus, no form of detasseling is presently entirely satisfactory, and a need continues to exist for alternatives which further reduce production costs and the eliminate self-pollination in the production of hybrid seed.

The laborious detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. Usually seed from detasseled normal maize and CMS produced seed of the same hybrid must be blended to insure that adequate pollen loads are available for fertilization when the hybrid plants are grown.

There can be other drawbacks to CMS. One is an historically observed association of a specific variant of CMS with susceptibility to certain crop diseases. This problem has led to virtual abandonment of use of that CMS variant in producing hybrid maize.

Another form of sterility, genic male sterility, is disclosed in U.S. Pat. Nos. 4,654,465 and 4,727,219 to Brar et al. However, this form of genetic male sterility requires maintenance of multiple mutant genes at separate locations within the genome and requires a complex marker system to track the genes and make use of the system convenient. Patterson also described a genic system of chromosonal translocations which are effective, but complicated. U.S. Pat. Nos. 3,861,709 and 3,710,511.

Many other attempts have been made to improve on these drawbacks. For example, Fabijanski, et al., developed several methods of causing male sterility in plants (see EPO 89/3010153.8 publication no. 329,308 and PCT application PCT/CA90/00037 published as WO 90/08828). One method includes delivering into the plant a gene encoding a cytotoxic substance associated with a male tissue specific promoter. Another involves an antisense system in which a gene critical to fertility is identified and an antisense to the gene inserted in the plant. Mariani, et al. also shows several cytotoxin encoding gene sequences, along with male tissue specific promoters and mentions an antisense system. See EP 89/401,194. Still other systems use "repressor" genes which inhibit the expression of another gene critical to male sterility. PCT/GB90/00102, published as WO 90/08829.

As noted, an essential aspect of much of the work underway with male sterility systems is the identification of genes impacting male fertility.

Such a gene can be used in a variety of systems to control male fertility. Previously, a male sterility gene has been identified in *Arabidopis thaliana* and used to produce a male sterile plant. Aarts, et al., "Transposan Tagging of a Male Sterility Gene in Arabidopsis", *Nature*, 363:715–717 (Jun. 24, 1993). In the present invention the inventors provide a novel DNA molecule and the amino acid sequence it encodes which is critical to male fertility in plants.

Further, the inventors present a unique variation to the method of controlling male sterility by using the DNA molecule to cause a plant to be male sterile after transformation, with fertility, not sterility, induced.

Thus, one object of the invention is to provide a nucleic acid sequence, the expression of which is critical to male fertility in plants.

Another object of the invention is to provide a DNA molecule encoding an amino acid sequence, the expression of which is critical to male fertility in plants.

A further object of the invention is to provide a method of using such DNA molecules to mediate male fertility in plants.

A still further object is to provide a method of mediating male fertility in plants by regulating expression of the DNA molecule naturally occurring in the plant.

Yet another object is to provide a method of mediating male fertility in plants by delivering the DNA molecule into a plant such that expression of the DNA molecule may be controlled.

Another object is to provide plants wherein male fertility of the plants is mediated by the DNA molecule.

A further object is to use plants having male fertility mediated by the DNA molecules in a plant breeding system.

Further objects of the invention will become apparent in the description and claims that follow.

SUMMARY OF THE INVENTION

This invention relates to nucleic acid sequences, and, specifically, DNA molecules and the amino acid encoded by the DNA molecules, which are critical to male fertility. It also relates to use of such DNA molecules to mediate fertility in plants. One such method is to controllably render plants male sterile by using an inducible promoter to regulate expression of the DNA molecule such that the gene is normally "off" and the plant is thus sterile. When the promoter is induced, the plant becomes fertile.

BRIEF DESCRIPTION OF THE DRAWINGS

FIG. 7 shows the nucleotide and amino acid sequence of fertile revertant plant DNA after Ac transposition.

DISCLOSURE OF THE INVENTION

All references referred to are incorporated herein by reference.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting.

MALE FERTILITY DNA MOLECULES

Genetic male sterility results from a mutation in one of the genes responsible for a specific step in microsporogenesis, the term applied to the entire process of pollen formation. These genes can be collectively referred to as male fertility genes. There are many steps in the overall pathway where a mutation can lead to male sterility. This seems aptly supported by the frequency of genetic male sterility in maize. New alleles of male sterility mutants are uncovered in materials that range from elite inbreds to unadapted populations. To date, published genetic male sterility research has been mostly descriptive. Some efforts have been made to establish the mechanism of sterility in maize, but few have been satisfactory. This should not be surprising given the number of genes that have been identified as being responsible for male sterility. One mechanism is unlikely to apply to all mutations.

The invention is of a plant male fertile gene. cDNA's specific for pollen development and tassel development have been extensively reported. To date, none of them have led to cloning a gene that can be referred to as impacting pollen development.

The following is presented by way of illustration and is not intended to limit the scope of the invention.

TAGGING

Figure 1:
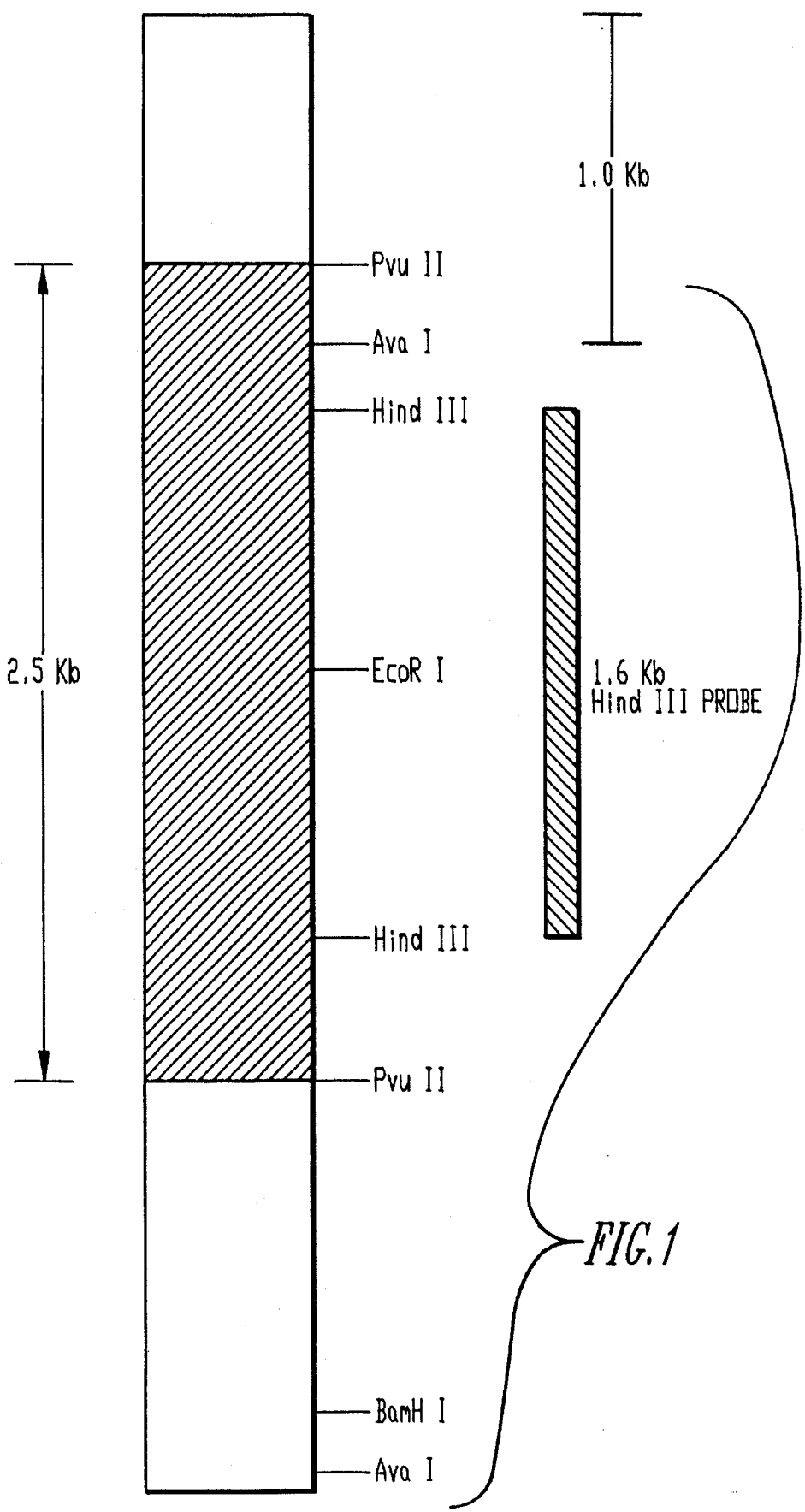
FIG. 1 is a restriction map of the transposon Ac.

Ac (Activator) is a well known transposable element first characterized in 1954 by Barbara McClintock, (McClintock, B., *Cold spring Harbor Symp. Quant. Biol.* 21:197–216 (1956); McClintock, B., *Carnegie Inst. Wash. Yrbook*, 53:254–260 (1954); see also Federoff, U.S. Pat. No. 4,732,856 issued Mar. 22, 1988 and Dooner, U.S. Pat. No. 5,013,658 issued May 8, 1991). Ac was used to clone this DNA molecule. A restriction map of Ac used here is depicted in FIG. 1. Those skilled in the art are familiar with the restriction sites of Ac. In sum, The Ac transposon went from the P-vv locus on chromosome 1 to chromosome 9. The only currently described male sterility gene on chromosome 9 is ms2, which has never been cloned or sequenced. See Albertsen, M. and Phillips, R. L, "Developmental cytology of 13 genetic male sterile loci in maize" *Canadian Jnl. of Genetics and Cytology* 23:195–208 (Jan, 1981). The only cloned fertility gene is the Arabidopsis gene described. Aarts, et al., supra. Test cross progeny have confirmed the genes are not allelic.

PLANT MATERIALS

Three maize lines were used, all of which are widely available to maize geneticists and regularly used by those skilled in the art and are described at Chen, et al., "Transposition of Ac from the P locus of maize into unreplicated chromosomal sites" *Genetics* 117:109–116 (September 1987). Such lines may be obtained, for example, from the authors of the above article, from Pioneer Hi-Bred International, Inc., or any one of many public sources such as the Maize Genetics Stock Cooperation Center, University of Illinois, Urbana/Champagne, Department of Agronomy S-123 Turner Hall, 1102 South Goodwin Avenue, Urbana, Ill., 61801.

The first line is W23P-vv. The P-vv allele is caused by the insertion of the mobile element Ac into the P locus. Emerson, R. "The inheritance of a recurring somatic variation in variegated ears of maize" *Am. Nat* 48:87–115 (1914); Brink, R. and Nilan, R. "The relation between light variegated and medium variegated pericarp in maize" *Genetics* 37:519–544 (1952) and Barclay, P. and Brink, R. "The relation between modulator and Activator in maize" *Proc. Nat'l. Acad. Sci.* U.S.A. 40:1118–1126 (1954). The P gene is a maize gene well characterized and fully detailed in the art. The P gene induces pigmentation of the pericarp in maize. Flavanone is reduced to phlobaphenes which cause pigmentation of the pericarp. One example of the detailed information on the P gene which is available to one skilled in the art is the discussion by Lechelt, et al., "Isolation and molecular analysis of the maize P locus," *Mol. Gen. Genet.* 219:225–234 (1989) and Chen, et al., "Molecular Analysis of Ac transposition and DNA replication" Genetics. This is an excellent marker gene because of its function in regulating the color of pericarp, and red striped pericarp results. The red stripes show the excision of Ac from P, restoring gene function and providing red pericarp.

The P-gene (P-vv) is on the same chromosome as known genetic male steriles previously mapped to chromosome 1. It has been shown that Ac transposes on the same chromosome 67% of the time. Van Schaik, N. V. and Brink, R. A., "Transpositions of modulator, a component of the variegate pericarp allele in maize" *Genetics* 44:725–738 (1959). However, this did not occur here, as the Ac transposed to chromosome 9. P-vv itself greatly facilitates transposon tagging because it is possible to visually observe when Ac has transposed from the P-gene and is elsewhere in the genome.

4C063 is a white inbred line that combines well with W23P-vv to give good hybrid plants with easily scored kernels. W22r-sc:m3 is a line with the Ds element at the R-locus. The plant is genetically dominant at all the anthocyanin pathway genes (A1, A2, Bz1, Bz2, C1, C2, Pr, R). Because Ds causes R to become dysfunctional, no anthocyanin are produced in the kernel.

This was coupled with use of W22r-sc:m3 stocks, in which Ds is integrated into the R-gene. The Ds element responds to the presence of Ac, by transposing to another site on the genome. It is, in fact, a defective Ac. The Ac transposon can move in and out of a gene on its own, whereas Ds cannot move unless Ac is present somewhere on the genome. The R gene is a gene in maize studied in considerable depth. It is known to encode enzymes required for synthesis of anthocyanin pigments. An example of the detailed information known regarding the R gene is the description and sequencing information found at Dellaporta, et al., *Stadler Symposium* 18:263 (1988) and Ludwig, et al., "Lc a member of the maize R gene family responsible for tissue-specific anthocyanin production, encodes a protein similar to transcriptional activators and contains the myc-homology region", *Proc. Nat. Acad. Sci.* 86:7092–7096 (Sept. 1989) and use of the gene as a visual marker, described at Bowen, et al., "R Genes as visual markers for corn transformation" Abstract edit. Gallagher, Academic Press (Oct. 1989) and Ludwig, et al., "A regulatory gene as a novel visible marker for maize transformation" *Science* 247: 449–450 (Jan. 26, 1990).

In the W22 r-sc:m3 stock, all kernel anthocyanin genes are dominant. The kernel color is yellow, however, because of Ds interrupting function of the R-gene. In the presence of Ac, however, the Ds element can transpose, resulting in purple-spotted kernels. Therefore, it was possible to 1) visually determine when Ac transposed away from the P-gene (red-striped or full red pericarp) and 2) determine whether Ac was still active (purple spots in the aleurone). By selecting either all red kernels or kernels with red pericarp stripes over the embryo that also have purple spots in the aleurone, it was possible to greatly enrich for those cases where an active Ac has transposed to another location in the the genome. By selfing plants resulting from these kernels, one can screen progeny families for any mutations affecting tassel or anther development. In this case, selfed families for the segregation of male-sterile plants were created.

CO-SEGREGATION ANALYSIS

Conducting co-segregation analysis for specific gene tagging and cloning strictly through a molecular approach can be tedious and time-consuming. The Ac-system, however, is well suited to co-segregation analysis at the field genetics level. Interaction between active Ac and Ds at the R-gene (r-sc:m3) can be utilized. Plants crossed with Ac were selfed and grown and those families segregating for male sterility identified. Once a family was identified that segregated for male sterility, additional seed was planted to cross with r-sc:m3 for co-segregation analysis. Each plant (fertiles and steriles) was crossed with r-sc:m3, the kernel color segregation observed on each ear and correlated with whether the plants were male fertile or male sterile.

A family was observed where the plants were mostly male sterile, with a few extruded abnormal anthers scattered about the tassel. In most cases, these abnormal anthers did not have pollen present. When every plant from this family was crossed with r-sc:m3, co-segregation of Ac with the male-sterile phenotype was observed as set forth in the table below.

TABLE 1

| Segregation of trhn-90-40 crossed with r:m3 | | | |
|---|---|---|---|
| Plant Phenotype | Ear Phenotype | Observed Number | Expected Number |
| Sterile | all kernels purple spotted | 8 | 8.25 |
| Fertile | ½ kernels purple spotted ½ kernels no spots | 16 | 16.50 |
| Fertile | all kernels | 9 | 8.25 |

TABLE 1-continued

Segregation of trhn-90-40 crossed with r:m3

| Plant Phenotype | Ear Phenotype | Observed Number | Expected Number |
|---|---|---|---|
| | no spot | | |

Male-sterile plants always produced ears with every kernel purple spotted. Two thirds of the fertile plants had ears that segregated 50% spotted kernels and 50% yellow kernels. One-third of the fertiles produced ears with all yellow kernels. This showed Ac had transposed into a gene responsible for male fertility and interrupted its function. The gene acts as a recessive, and when homozygous, results in male sterility. This segregation was verified in further plantings.

MOLECULAR ANALYSIS

Southern analysis was carried out to confirm association of Ac with sterility. Southern analysis is a well known technique to those skilled in the art. This common procedure involves isolating the plant DNA, cutting with restriction endonucleases and fractionating the cut DNA on an agarose and transferring to nitro cellulose membranes to separate the DNA by molecular weight. It was then hybridized with the probe fragment which was radioactively labeled with P32 and washed in an SDS solution. Southern, E., "Detection of a specific sequences among DNA fragments by gel electrophoresis," *J. Mol. Biol.* 98:503–517 (1975).

DNA was isolated from sterile-crossed progeny and fertile-crossed progeny, keeping the purple-spotted kernel seedlings separate from the yellow kernel seedlings. DNA was isolated from the top two leaves of one month old plants using an Urea procedure as described at Dellaporta, et al., "A plant DNA minipreparation: version II" *Plant Mol. Bio. Rep.* 1:19–21 (1983). The isolated DNA was cut with PvuII in order to find a 2.5 kb fragment only associated with Ac as shown in the restriction map (FIG. 1). Approximately 8 ug of DNA was digested with the appropriate enzyme according to the manufacturer's instructions (Promega). DNA digests were electrophoresed through a 0.75% Sea Kem GTG agarose gel and transferred to Duralon-UV nylon membrane by capillary blotting and fixed to the membrane by baking 1 hour at 85C. The 1.6 kb HindIII fragment of Ac was used as a probe in the Southern Blot analysis.

Figure 2:
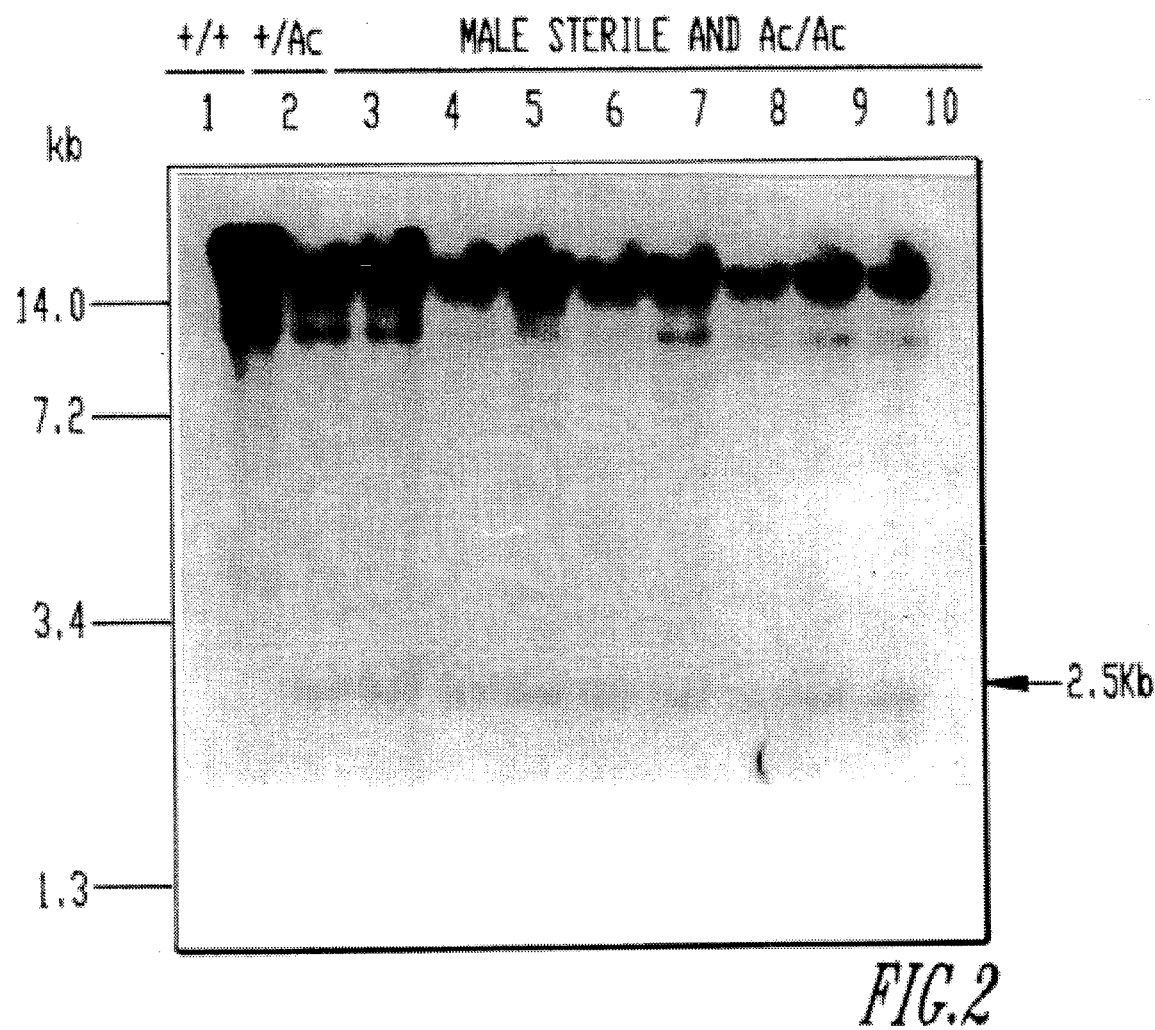
FIG. 2 is a gel of a Southern Blot analysis of PvuII digested DNA from an Ac family segregating for sterility and hybridized with an internal 1.6 kb HindIII from Ac.

The results are shown in the gel at FIG. 2. At FIG. 2, the male steriles are lanes 3–10. Lane 2 is the heterozygous fertile plant and lane 1 the wild type. As this gel confirms, a 2.5 kb fragment band appeared in all sterile (purple spotted kernels) plants and did not appear in any of the fertile (yellow kernels) plants. This confirms the Ac was either closely linked to the male fertility locus or inserted into the locus, inhibiting the function of the gene and resulting in a male sterile phenotype.

CLONING

The DNA adjacent to the known Ac sequence was cloned and used in obtaining the entire gene.

To summarize, the male fertile plant DNA and the male-sterile plant DNA were digested with restriction endonucleases Pst I, Eag I, Sal I, Sac I, and Xba I to locate a single band with the Ac element. Fragments were electrophoresed, Southern transferred, and hybridized with the Ac HindIII fragment. A 6 kb PstI fragment was indentified that co-segregated with male-st element. The inverse PCR method of Baker et al was used to isolate the DNA associated with Ac. Earp, D. J. Lowe, B. and Baker B., "Amplification of genomic sequences flaking transposable elements in host and heterologous plants: a tool for transposon tagging and genomic characterization," *Nucleic Acids Research* 18:3271–3279 (1990).

Figure 3:
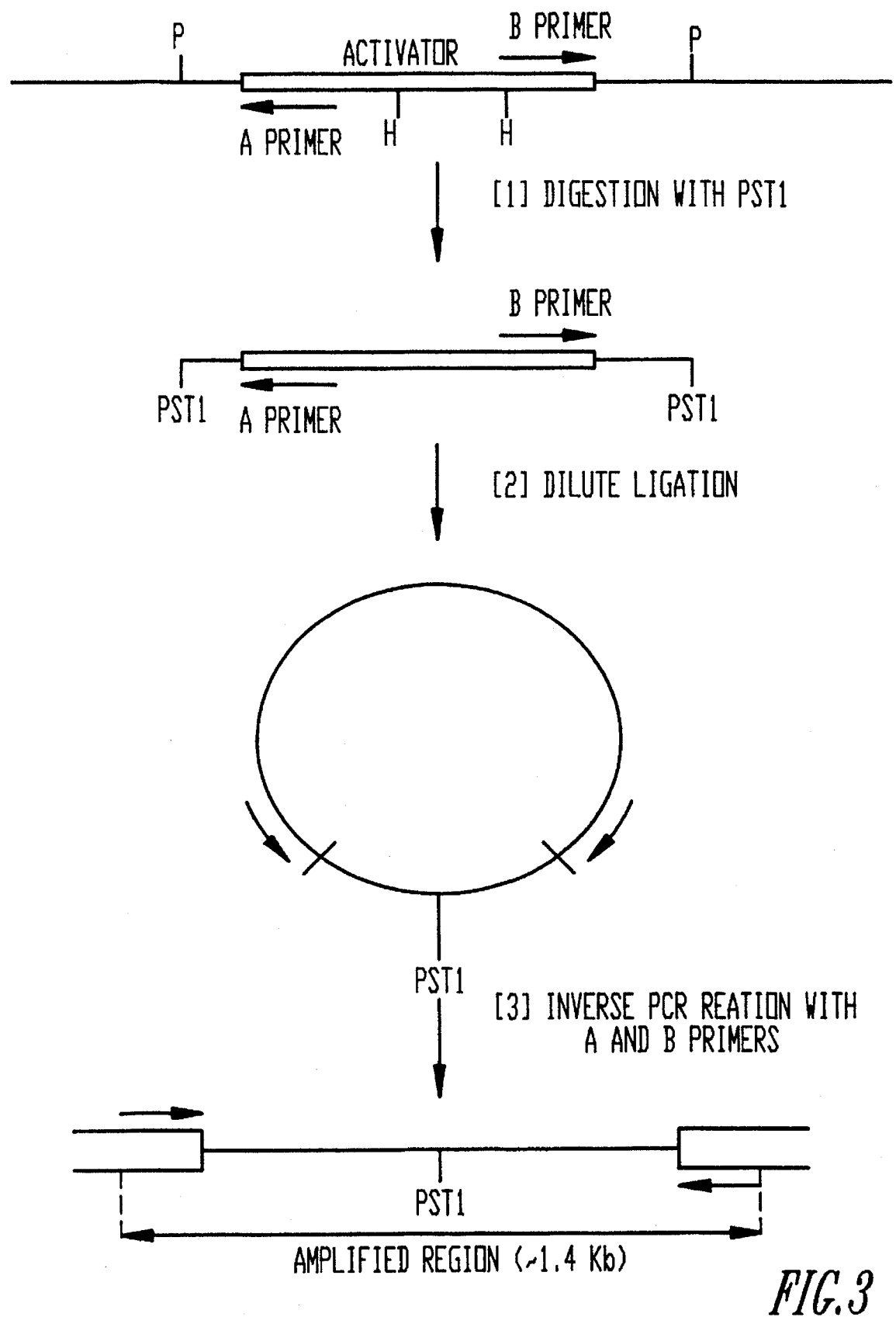
FIG. 3 is a schematic representation of inverse polymerase chain reaction.

A schematic depicting the well known inverse polymerase chain reaction procedure is shown in FIG. 3. After obtaining the 6 kb fragment, the ends were religated. A and B primers were identified readily since the sequence of Ac is known. Thus the 5' and 3' oligonucleotides could be identified, and, according to the inverse PCR technique, react to amplify the intervening sequences. The A and B primers were run from each side of the religated circle where the Ac had been. In this way, the DNA between the end of the Ac was amplified and a 1.3 kb segment of DNA isolated. The known 4.8 kb Ac fragment plus the amplified 1.3 kb IPCR product nearly equaled the 6.0 kb Pst I fragment isolated previously.

Details of this above summarized procedure are as follows. Genomic DNA was isolated as described above. 20 ug of DNA was digested with 20 units of PstI according to the manufacturer's instructions (Promega). The digested DNA was electrophoresed as described above using a preparative comb. A gel fragment, which contained DNA with a molecular weight between 5.5 and 6.5 kilobases, was excised from the gel. The DNA was electro-eluted from the agarose by using Spectra/Por membrane #2, MWCO 12-14000 (Spectrum Medical Industries, Inc.) which contained 0.4 ml sterile water and electrophoresing against 1X Tris-Acetate buffer pH 8.0 (TAE). The isolated DNA was extracted consecutively with Tris-equilibrated phenol pH 7.0:chloroform (1.1), chloroform, then ethanol precipitated, dried and resuspended in sterile water. Ligations were performed according to the manufacturer's instructions (Bethesda Research Laboratories) using the Psi digested genomic DNA at a final concentration of 20 ng/u. Ligations were done 18 hours at 14C.

Oligonucleotide primers were synthesized on an Applied Biosystems model 394 DNA/RNA synthesizer. Primer B5 was essentially the same as described by Earp et al., supra, except for an EcoRI site engineered at the 5' end and an extra two bases at 3' end. The sequence of both primers used in the Ac inverse PCR reaction are as follows:

A5: 5' GATAGAATTCGGTACGGGATTTTCCCATCCTACTT 3'

B5: 5' GGTAGAATTCGTTTTCGTTTCCGTCCCGCAAGTT 3

PCR was carried out using 25 ng of circularized genomic template DNA in a reaction containing 2 uM of each primer, 0.24 mM of each dNTP, 3 units of Hot Tub polymerase (Amersham) in a 1X reaction buffer supplied by the manufacturer. Amplification was performed in a MJ Research Inc. model PTC-100-96 thermocycler under the same conditions as described by Earp et al., supra. Reaction products were electrophoresed on 1% LMP agarose gels (Bethesda Research Laboratories). The amplification product was isolated from the gel using a Magic PCR kit (Promega) and reamplified using the above conditions.

cDNA ISOLATION cDNA library screenings are commonly known among those skilled in the art, and are described at Mariatis T. et al., Molecular Cloning: A Laboratory Manual, Cold Spring Harbor Laboratory, Cold Spring Harbor, N.Y.). Libraries were created as follows. RNA from *Z. mays* tassels was isolated using a guanidine thiocyanate method followed by banding in a cesium chloride gradient. Poly A+RNA was selected using oligo dT cellulose. Two cDNA libraries were constructed in the vectors pCDNAII (Invitrogen) and Uni-Zap XR (Stratagene) using 5 ug of mRNA for each according to the manufacturer's instructions.

Figure 4:
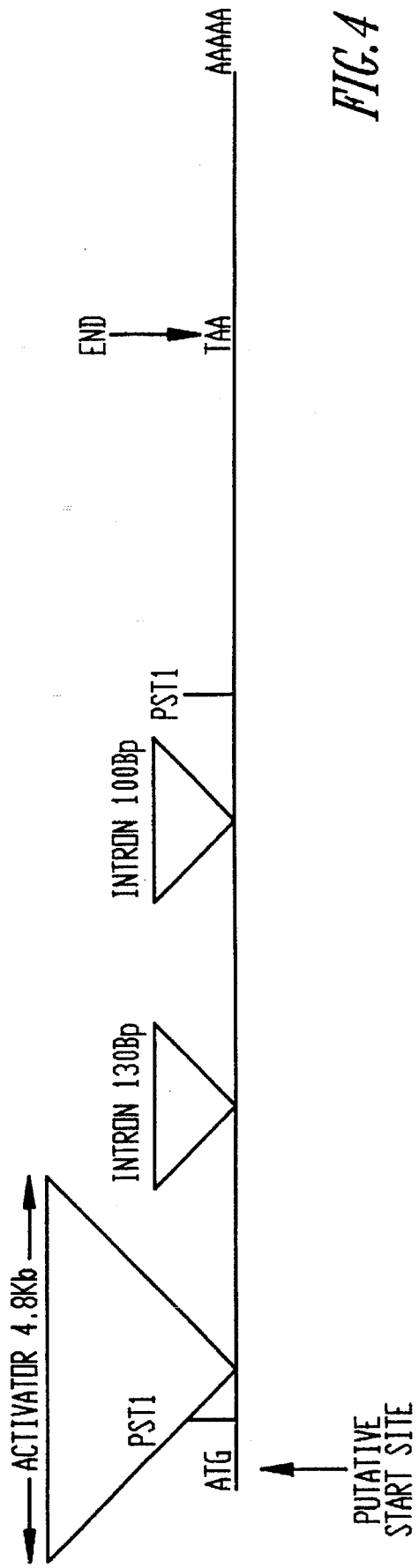
FIG. 4 is a graphic representation of the 1.4 kb DNA isolate and its intervening sequences.

The 1.3 inverse PCR product was probed onto the arrayed cDNA tassel library of about 1000 clones and from this a single homologous clone with an insert size of about 1.4 kb obtained. It was 1550 base pairs and is graphically depicted in FIG. 4. The genomic piece will, of course, vary according to the background of the plant from which it is isolated and the introns may or may not be present. This, however, shows how the Ac element appeared in this isolate.

Figure 5:
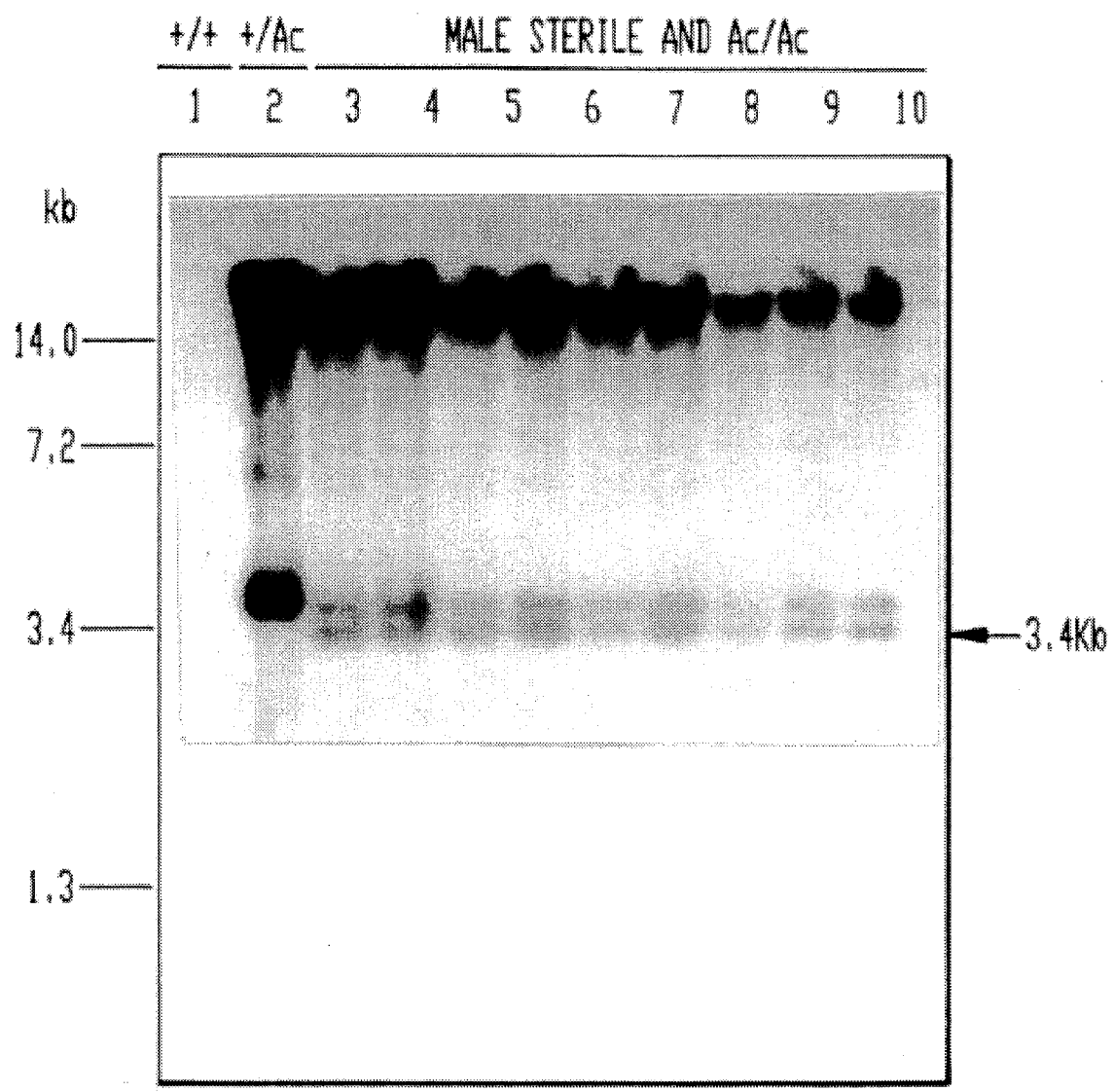
FIG. 5 is a Southern Blot analysis gel of PvuII digested DNA of an Ac family segregating for sterility and hybridized with the 1.4 kb DNA isolate.

The 1.4 kb was hybridized to the PvuII segregation membrane to insure the 3.4 kb co-segregating band found with the inverse PCR product was a new genomic region and not small amounts of Ac DNA contained on the ends of the fragment. The results are shown in the gel in FIG. 5. As can be seen, the 1.4 kb from the library hybridized in sterile plants to the same 3.4 kb fragment that co-segregated with the male sterile phenotype and the purple spotted kernels plants from the fertile heterozygous.

The 1.4 kb segment was then used against a second cDNA tassel library and the full length cDNA was obtained, and named MS45.

NORTHERN ANALYSIS

Figure 6:
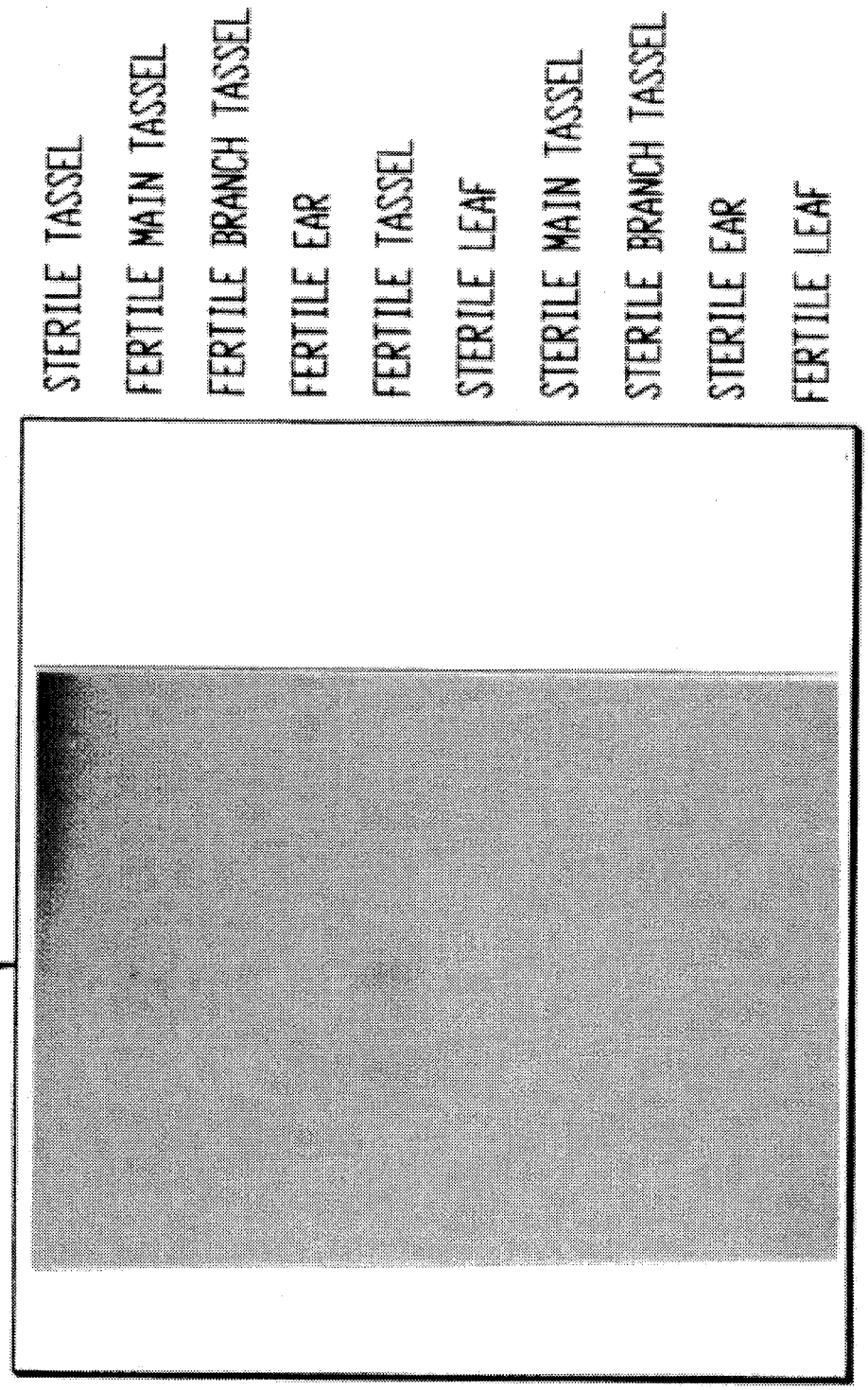
FIG. 6 is a Northern Blot analysis gel hybridized with the male fertility gene MS45.

Tissue from tassels, ears and leaves of sterile and fertile plants was isolated as described previously, and a Northern Blot analysis run on the extracts. Northern analysis is also a commonly used technique by those skilled in the art and is similar to Southern analysis except that RNA is isolated and place on an agarose gel. The RNA is then hybridized with a labelled probe. Potter, E., et al., "Thyrotropin releasing hormone exerts rapid nuclear effects to increase production of the primary prolactin mRNA transcript," *Proc. Nat. Acad. Sci.* U.S.A. 78:6662–6666 (1981); Lechelt, et al., supra. Total RNA was isolated from 1) leaves of plants grown approximately 2 months; 2) tassels at roughly the mid-vaculate stage; and 3) immature ears between 4.5–5.0 cm in length. Tissue was ground in liquid nitrogen then sequentially treated with a detergent extraction, a differential LiCl precipitation, and an ethanol precipitation. The gel was hybridized with the MS45cDNA isolated as described above. The cDNA hybridized only with DNA from fertile tassels as can be seen in FIG. 6.

REVERTANTS

To further confirm the gene as one critical to male fertility, revertants were identified. Since it would not be possible to distinguish normally fertile plants from revertants, plants were selected that showed sterility, but shed some pollen. These were crossed as males to unrelated lines and no male sterile plants resulted. The MS45 cDNA was recovered and analyzed to find the Ac had left a "footprint" when transposing out of the gene of six base pairs, keeping the sequence in frame. See FIG. 7, showing two amino acids are added, but the frame does not shift.

RFLP MAPPING

Figure 8:
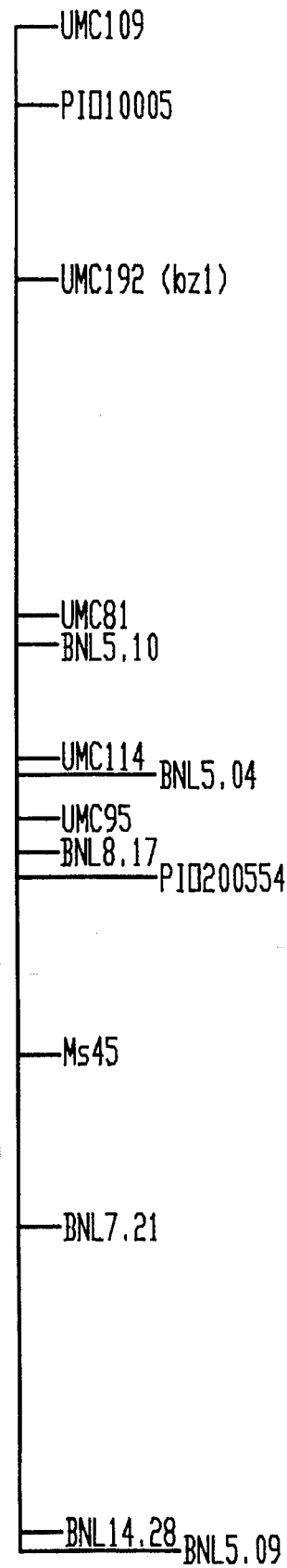
FIG. 8 is an RFLP map of chromosone 9 showing the male fertility gene MS45.

The IPCR fragment was RFLP-mapped in a B73×Mo17 F2 population. It mapped to chromosome 9L between probes and Burr 7.21 as described in Maize Genetics Cooperation Newsletter, 67:165 (Mar. 15, 1990) and depicted in FIG. 8.

SEQUENCING

Sequencing of the MS45 clone was accomplished using the dideoxy chain termination method of Sanger, et al., *Proc. Nat. Acad. Sci.* U.S.A. 74:5463–5464 (1977).

By referring to MS45 DNA, it is to be understood that what is meant is a DNA sequence as set forth below which produces the amino acid sequence also set forth below. One skilled in the art readily appreciates that more than are three member codon may encode the same amino acid sequence.

METHODS OF CONTROLLING MALE FERTILITY WITH MS45 DNA

It is evident to one skilled in the art that the DNA described herein can be used in any one of a wide variety of methods to control male fertility in plants. The following are presented by way of illustrating several of these methods and are not intended to limit the possible uses of the DNA molecules herein described, nor the scope of the invention.

Once one has a DNA molecule that is critical to male fertility in plants, it is possible to create a sequence which is in inverse orientation to the 5' to 3' normal orientation of that DNA sequence. When this antisense molecule is delivered into the plant, it prevents normal expression of the male fertile sequence. It is believed the antisense DNA transcribes to produce an RNA which is complimentary to and capable of hybridizing to the mRNA produced by the male fertility gene and thus inhibit translation. The protein coded for by the mRNA is not produced and cannot play its role in male fertility. With the male fertility gene described herein, a construct is delivered to the plant having the MS45 DNA therein, the construct having a transcriptional promoter segment, a transcriptional termination segment and a DNA segment producing an ribonucleotide sequence complimentary to a ribonucleotide sequence of the MS45 DNA.

This use of antisense to inhibit or control expression of a gene is known to one skilled in the art and is described in detail at Inouye, U.S. Pat. No. 5,190,931, issued Mar. 2, 1993. In one embodiment, the inventors there describe cutting the DNA with restriction endonucieases, to result in a religated plasmid having lost a fragment between two restriction sites and into which another DNA fragment may be inserted. The normal DNA is digested, purified and a fragment inserted in opposite orientation. They thus inhibited expression of lpp, OmpA and OmpC in bacteria and controlled the development of coliphage SP using such constructs. An antisense RNA complimentary to the 5' leader region of the OmpA RNA, but not encompassing the Shine-Dalgarno sequence was less effective than a transcript covering the ribosome binding site and initiating codon. An extensive view of antisense regulation is provided by Claude Helene and Jean-Jacques Toulme in a review, "Specific regulation of gene expression by antisense, sense and anti-gene nucleic acids," *Biochemica et Biophysica Acta* (1990) 99–125.

Another example of antisense and its use in inhibition or control of a gene include antisense constructs to genes encoding flavonoid biosynthesis in anthers to provide male sterility. Vander Meer, et al., "Antisense inhibition of flavonoid biosynthesis in petunia anthers results in male sterility," *The Plant Cell*, 4:253–262 (March 1992). Antisense chalcone synthesis genes with homologous sequences to other genes expressed in anthers and a CaMV355 promoter result in male sterile white pollen. As can be seen, use of antisense to control gene expression is well known. See also e.g. Bourque, June E. and Folk, William R., "Suppression of gene expression in plant cells utilizing antisense sequences transcribed by RNA polymerase II", *Plant Molecular Biology*, 19:641–647 (1992); Weintrab, et al., *Trends Gen.* 1:22–25 (1985).

Another method of controlling gene expression is by modification of transcriptional activators. During gene expression, the double stranded DNA is transcribed to a corresponding single-stranded messenger RNA. The sense strand separates from its antisense partner and enzymes assemble an RNA molecule that compliments the sequence on the antisense strand. The mRNA migrates to ribosomes which read the encoded information to produce amino acids.

Transcription of eukaryotic genes is influenced by various elements, including, transcriptional regulatory proteins which bind to the DNA in a sequence-specific manner. These transcriptional activators may be modified so that they bind to the DNA, but cannot perform their normal activator function. Transcriptional activators have two domains, a binding domain, and an activation domain. By altering the amino acid sequence of the transcriptional activator proteins for a gene, providing a DNA sequence which codes for the same, and delivering that DNA into the plant, expression of the target gene may be blocked. See Goff, S. A. et al. "Transactivation of the Anthocyanin pathway structural genes with wild-type and altered cl proteins" *Maize Genetics Cooperation Newsletter* 64:6 (Mar. 1, 1990).

A variation on this method is the isolation of genetic suppressor elements encoding dominant negative mutant proteins or inhibitory antisense RNA by random DNA fragmentation and identified by functional selection for the phenotype associated with suppression of the target. This is what Holzmayer, et al. described in their article, "Isolation of dominant negative mutants and inhibitory antisense RNA sequences by expression selection of random DNA fragments" *Nucleic Acids Research*, Vol. 20, No. 4, 711–717 (Dec. 3, 1991). There they randomly fragmented bacteriophage lambda DNA to protect *E. coli* cells from lambda-induced lysis. Multiple genetic suppressor elements were isolated encoding either protein or antisense RNA fragments.

Inhibition of normal gene expression has also been observed when additional or over expression of an endogenous gene was found to suppress gene expression. This "sense inhibition", sometimes referred to as "co-suppression", has been well documented. See e.g. Brussian, et al., "An Arabidopsis mutant with reduced level of cab 140 RNA is a result of cosuppression", *The Plant Cell*, 5:667–677 (June, 1993); Vander Krol et al., "Flavonoid genes in Petunia: addition of a limited member of gene capus may lead to suppression of gene expression" *The Plant Cell* 2:291–299 (April 1990).

Other means of negative control regulation include repression of gene transcription. In one system factors contain DNA binding domains but lack functional activation domains, competing with activators for binding to the same sites and blocking activation. Others heterodimerize with activators reducing either their DNA-binding affinity or ability to activate transcription. Still other repressors interact with activator factors when bound to DNA and block transactivation function. A further type of down-regulators comprises inhibitory proteins that sequester the activator in a complex that is unable to bind DNA. See reviews by Jackson, M. E., *J. Cell Sci.* 100:1–7 (1991); Jones, N., *Curr. Biol.* 1:224–226 (1991); Mitchell. P. J. and Tjian, R., *Science* 245:371–378 (1989).

Direct mutation of the endogenous gene itself will also change the male fertility gene to a male sterility gene. Irradiation causes breakage and rearrangement of the chromosomes and modification of the composition of individual genes. Exposure to x-rays is a method of gene mutation well known for sometime. See e.g., Stadler, L. J. "On the genetic nature of induced mutations in plants," Reprint, Proceedings of the Sixth International Congress of Genetics, Vol. 1, 274–294 (1932). Other techniques include exposure to chemical mutagens such as ethyl methanesulfonate, and N-methyl-N-nitro-N-nitrosoguanidine, as was accomplished by Neuffer, M. G., and Coe Jr., E. H. on pollen grains and described in their early work at "Paraffin oil technique for treating mature corn pollen with chemical mutagens" *Maydica* XXIII (1978) 21–28; also, see Thurling, N. & Depittayanan, "EMS induction of early flowering mutants in spring Rape (*Brassica napus*)" *Plant Breeding* 108:177–184 (1992). Other methods include treatment with sodium azide (Rao, B. "A case of genic male sterility induced by sodium azide in Pearl Millet", Biol. Zentralbl. 104:579–521 (1985); Conger, B. V. and Carabia, J. V. "Mutagenic effectiveness and efficiency of sodium azide versus ethyl methanesulfonate in maize: induction of somatic mutations at the $yg_2$ locus by treatment of seeds differing in metabolic state and cell population" *Mutation Research* 46:285–296 (1977)) and exposure to gamma radiation (Filippetti, A. and DePace, C., "Improvement of seed yield in *Vicia falsa* L. by using experimental mutagenesis II comparisons of gamma-radiation and ethyl-methanesulfonate (EMS) in production of morphological mutants" *Euphytica* 35:49–59 (1986)).

Thus, it is clearly evident to one skilled in the art, that a male fertility gene, once identified, can be used in a variety of methods to mediate male fertility in plants. The foregoing illustrates but a few such methods which can be used with a novel male fertile gene. Yet one more novel method is described below created by the inventors of this application.

CONSTITUTIVE MALE STERILITY METHOD

This invention differs from conventional approaches to male sterility in plant breeding and seed production in that an inducible promoter is used to regulate expression of the gene which is known to be critical to plant male fertility. The first step in the practice of this invention is therefore the selection of a gene on which fertility is dependent. One type are the MS45 DNA molecules described, supra.

The selected gene is cloned, its native promoter enabled, and the modified gene is inserted into an expression sequence with an inducible promoter responsive to external control. Preferably, the promoter is one which responds to application of a specific non-phytotoxic chemical to the plant.

Using transformation and gene substitution, the gene is inactivated in the genome of the plant and replaced by the genetically-engineered gene incorporated into the expression sequence with the inducible promoter.

This invention is unique in that the process results in using the inducible promoter to induce fertility, not sterility. In this invention, the selected gene's promoter sequences are removed so that the gene is not transcribed and the plant is male sterile. When it is desired to increase the male-sterile plant, male fertility is restored by inducing expression of the critical gene. In the preferred embodiment this is accomplished by treating growing male sterile plants with a specific non-phytotoxic chemical.

Induction of the inducible promoter by chemical treatment will be dependent on various factors associated with the chemical treatment itself and various environmental conditions at the time of treatment. If the critical gene were normally "on," to be inactivated by chemical treatment, a treatment failure would result in self-pollination and production and sale of inbred, rather than hybrid seed. Seed laws that govern the sale of hybrid seed require a high degree of seed purity such that percentages of seed that do not conform to the hybrid specification must be kept very low. Because one maize plant can produce in excess of six million pollen granules, even a limited treatment failure could result in a high percentage of self-pollination. For these reasons, the present invention is practiced in such a manner that the gene is normally "off" and the corresponding trait is not expressed, so that under normal conditions self-pollination cannot occur. In addition, by having the critical gene normally "off," chemical treatment is not necessary in the large-scale production of hybrid seed, so that chemical usage (and associated expense) is minimized and the risk of treatment failure is present only in the carefully controlled, limited scale production of parent seed, where self-pollination is desired. Since treatment failure in such a case results in underproduction of pollen, and since pollen is normally overproduced by a wide margin, the process of this invention for production of parent seed will tolerate a treatment failure rate as high as 70% to 80% with minimal effects on yield of parent seed.

In general, in accordance with the invention described herein, the DNA molecule herein described is incorporated into the plant along with a necessary promoter which is inducible. The plant will be sterile since the DNA molecule is not expressed and when the promoter is induced, the plant will be fertile. The native gene producing the DNA molecule product is a normally fertile plant which may be inactivated by any of a variety of methods described below, such as backcrossing or homologous recombination.

INDUCIBLE PROMOTERS

In the practice of this invention the promoter region is removed from a cloned gene responsible for male fertility and is replaced with a promoter that only responds to a specific external stimulus. Thus, the gene will not be transcribed except in response to the external stimulus. As long as the gene is not being transcribed, its gene product—which is necessary for completion of pollen development—is not produced. This causes a breakdown in one or more of the biochemical/physiologic pathways of pollen development, which results in male sterility. The plant can only become fertile under the specific stimulus that activates the selected promoter.

An example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Wiegand, et al., "Messenger RNA Encoding a Glutathione-S-Transferase Responsible for Herbicide Tolerance in Maize is Induced in Response to Safener Treatment", *Plant Molecular Biology* 7: 235–243, 1986). It has been discovered that treating maize seed with GSTs increases the tolerance of the maize to the herbicides. Studies have shown that the GSTs are directly involved in causing this enhanced tolerance. This action is primarily mediated through a specific 1.1 kb mRNA transcription product. In short, maize has a naturally occurring quiescent gene already present that can respond to GSTs and that can be induced to produce a gene product. This gene has already been identified and cloned. Thus, in one embodiment of this invention, the promoter is removed from the GST responsive gene and attached to the male fertility gene that previously has had its native promoter removed. This engineered gene is the combination of a promoter that responds to an external chemical stimulus and a gene responsible for successful development of fertile pollen.

GENE INTRODUCTION

Several methods are known in the art for transferring cloned DNA into maize. These include electroporation-facilitated DNA uptake by maize protoplasts (Rhodes et al., "Genetically Transformed Maize Plants from Protoplasts", *Science*, Vol. 240 (8 Apr. 1988); treatment of maize protoplasts with polyethylene glycol (Lyznik et al., "Stable Co-Transformation of Maize Protoplasts with Gus A and Neo Genes", *Plant Molecular Biology* 13: 151–161, 1989); and bombardment of maize cells with DNA laden microprojectiles (Klein, et al., "Genetic Transformation of Maize Cells by Particle Bombardment", *Plant Physiol.* (1989) 91, 440–444) and Klein, et al., "Factors Influencing Gene Delivery into *Zea mays* Cells by High-Velocity Microprojectiles", *Bio/Technology* Vol. 6, May 1988).

Each of these techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. A commonly used selectable marker gene is neomycin phosphotransferase II (NPTII). This gene conveys resistance to kanamycin, a compound that can be added directly to the growth media on which the cells grow. Plant cells are normally susceptible to kanamycin and, as a result, die. The presence of the NPTII gene overcomes the effects of the kanamycin and each cell with this gene remains viable. Another selectable marker gene which can be employed in the practice of this invention is the gene which confers resistance to the herbicide glufosinate (Basta). A screenable gene commonly used is the β-glucuronidase gene (GUS). The presence of this gene is characterized using a histochemical reaction in which a sample of putatively transformed cells is treated with a GUS assay solution. After an appropriate incubation, the cells containing the GUS gene turn blue. Another screenable gene is a transcriptional activator for anthocyanin biosynthesis, as described in Bowen, et al., "R Genes as visual markers for corn transformation" Abstract edit. Gallagher, Academic Press (Oct. 1989); Ludwig, et al., "A regulatory gene as a novel visible marker for maize transformation" *Science* 247: 449–450 (Jan. 26, 1990). This gene causes the synthesis of the pigment anthocyanin. Cells transformed with a plasmid containing this gene turn red. Preferably, the plasmid will contain both selectable and screenable marker genes.

The plasmid containing one or more of these genes is introduced into either maize protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

INACTIVATION OF NATIVE GENE

It will be readily appreciated by those skilled in the art that a wide variety of methods are known to disable the native gene. Homologous recombination is but one of the methods known to those skilled in the art for rendering a native gene inoperative. Thus, when the engineered gene is homologously recombined into the plant, the native gene will be rendered inoperative. A good overview of this general process is provided by Yoder, J. I., and Kmic, Eric, in "Progress Towards Gene Targeting in Plants", *Genetic Engineering,* Vol. 13 (Plenum Press, New York, 1991). At page 265 of this reference, the authors note "gene targeting can be used to silence or replace the endogenous gene with an engineered allele; thus the phenotype of the altered gene, or its regulatory sequences, can be evaluated in planta." It is pointed out that genetic recombination takes place through breakage and reunion of DNA and the rejoining mechanism pairs the complimentary DNA sequences. (See, e.g. 271, supra).

A further discussion of intrachromosomal homologous recombination in plants is discussed at Peterhans, A., Schlupmann, H., Basse, C. and Paszkowski, J., "Intrachromosomal Recombination in Plants", *The EMBO Journal,* Vol. 9, No. 11, pp. 3437–3445, 1990.

A variety of different means, in addition to these specific examples, would be available to one skilled in the art. A still further example includes backcrossing, using generally accepted plant breeding techniques, to in effect "delete" the native gene. Backcrossing is often used in plant breeding to transfer a specific desirable trait from one inbred or source to an inbred that lacks that trait. This can be accomplished for example by first crossing a superior inbred (A) (recurrent parent) to a donor inbred (non-recurrent parent), which carries the appropriate gene(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred. A result of any backcrossing method is that the "native" gene is replaced by the desired gene.

A unique method is discussed in the 1991 Science magazine, reporting on prior work relating to using "transgenic scissors". This article describes a method in which scientists may remove a marker gene which is attached to a gene having a desired trait in a plant. The "scissor," according to this method, is an enzyme obtained from a bacterial virus known as "Cre" for control of recombination. *Science,* p. 1457, 6 Dec. 1991. The enzyme is capable of snipping out any DNA located between a pair of 34-base pair sequences, called lox, for locus of crossing over. This is described in further detail in the patent application filed by Du Pont, and published at WO 91/09957.

STERILITY SELECTION AND FERTILITY RESTORATION

After the gene is introduced into a plant, the appropriate plant types are selected, that is plants that are male sterile. These plants are male sterile because the isolated and cloned male fertility gene does not have its native promoter and, therefore, is not producing its gene product that is crucial to successful pollen development. Therefore, the engineered gene acts as a recessive mutant allele of that gene. In normal plant biotechnology, once the desired genotype is identified following transformation and regeneration, the plants are selfed to recover that genotype. However, in the practice of this invention, the desired genotype cannot be selfed at the first generation because it is male sterile. To obtain progeny, fertility must be induced by spraying the plants with a compound which induces transcription of the gene by activating the altered promoter. In the case of the GST promoters, the compound is preferably a GST-inducing compound such as N,N-diallyl-2-2-dichloroacetanide. The promoter attached to the male fertility gene responds to this chemical and causes the transcription of the gene to begin. Once this occurs, the normal gene product is produced from the gene and some level of male fertility is induced. Pollen from this plant is then used to effect pollination of the original selected genotype.

Once the initial isolation and propagation of the desired genotype is completed, the procedure is more straightforward. Only inbreds that are used as female parents in hybrid crosses are transformed into male sterile variants. Once they are transformed, the amount of male sterile/female fertile seed must be increased. This is accomplished by planting in an isolated area (away from other maize pollen) and spraying with a chemical to which the promoter responds. Spraying induces the promoter to start transcription of the gene attached to it. This will produce some degree of fertility. A particular advantage of this system in comparison to systems such as that disclosed in PCT publication WO89/10396 of Mariani et al (based on Intl. Appl. No. PCT/EP89/00495), in which sterility is induced, is that the treatment does not have to be 100% effective, because normally much more pollen is produced by a maize plant than is actually needed for fertilization of all available silks. Therefore, even low fertility restoration will be effective in obtaining acceptable levels of seed increase. At the same time, self-pollination does not occur in hybrid seed production because the plants of this invention are normally male sterile and must be treated to become fertile. In systems in which sterility is induced, induction of sterility must be 100% effective to avoid self-pollination when hybrid seed is produced.

All the seed harvested continues to be homozygous and sterile since the fertility is only restored in a single parent generation by treatment with the fertility inducing chemical. This seed is then used in a hybrid production field where it is used as a female parent. Because the plants are male sterile, they do not have to be detasseled. All of the hybrid plants produced from such seed are male fertile because the resulting progeny inherit one modified gene from the female parent and one normal gene from the male parent. Normal pollen production occurs.

While the foregoing illustrates the preferred embodiment of the invention, it will be appreciated that various changes can be made without departing from the spirit and scope of the invention.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 1419 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
GAATTCGGCA CGAGGTCCAC CAGCATGGAG GAGAAGAGGA AGCTGCAGTG GCGGCGAGGG      60
CGTGATGGCA TCGTGCAGTA CCCTCACCTG TTCTTCGCGG CCCTGGCCCT GGCCCTCCTA     120
GTCGCGGACC CGTTCGGCCT CAGTCCGCTG GCCGAGGTCG ACTACCGGCC GGTGAAGCAC     180
GAGCTCGCGC CGTACGGGGA GGTCATGGGC AGCTGGCCCA GAGACAATGC CAGCCGGCTC     240
AGGCGCGGGA GGCTGGAGTT CGTCGGCGAG GTGTTCGGGC GGAGTCCAT CGAGTTCGAT      300
CTCCAGGGCC GCGGGCCGTA CGCCGGCCTC GCCGACGGCC GCGTCGTGCG GTGGATGGGC     360
GAGGAGGCCG GGTGGGAGAC GTTCGCCGTC ATGAATCCTG ACTGGTCAGA AGAAGTCTGT     420
GCCAATGGAG TGAACTCAAC GACGAGGAAG CAGCACGAGA AGGAGGAGTT CTGCGGCCGG     480
CCGCTCGGCC TGAGGTTCCA CGGGGAGACC GGCGAGCTCT ACGTCGCCGA CGCGTACTAC     540
GGTCTCATGG TCGTTGGCCA GAGCGGCGGC GTGGCGTCCT CCGTCGCGAG GGAAGCCGAC     600
GGGGACCCCA TCCGGTTCGC GAACGACCTC GATGTGCACA GGAATGGATC CGTATTCTTC     660
ACTGACACGA GCATGAGATA CAGCAGAAAG GACCATCTGA ACATCCTGTT AGAAGGAGAA     720
GGCACCGGGA GGCTGCTCAG GTACGATCCA GAAACAAGTG CTGTCCATGT CGTGCTCAAG     780
GGACTGGTGT TCCCAAACGG CGTGCAGATC TCAGAAGACC ATCAGTTTCT TCTCTTCTCC     840
GAGACAACAA ACTGCAGGAT AATGAGGTAC TGGCTGGAAG GCCCAAGAGC GAGCGAGGTA     900
GAGGTGTTCG CGAACCTGCC GGGCTTCCCC GACAACGTGC GCTCCAACGG CAGGGGCCAG     960
TTCTGGGTGG CGATCGACTG CTGCCGGACG CCAGCGCAGG AGGTGTTCGC CAAGAGGCCG    1020
TGGCTCCGGA CCCTGTACTT CAAGTTCCCG CTGTCGCTCA AGGTGCTCAC TTGGAAGGCC    1080
GCCAGGAGGA TGCACACGGT GCTCGCGCTC CTCGACGGCG AAGGGCGCGT CGTGGAGGTG    1140
CTCGAGGACC GGGGCCACGA GGTGATGAAG CTGGTGAGCG AGGTGCGGGA GGTGGGCAGC    1200
AAGCTGTGGA TCGGAACCGT GGCGCACAAC CACATCGCCA CCATCCCCTA CCCTTTAGAG    1260
GACTAACCAT GATCTATGCT GTTTCAATGC CTCCTAATCT GTGTACGTCT ATAAATGTCT    1320
AATGCAGTCA CTGGTTGTAA TCTTGTTTGT GTTTGGCAAA TTGGCATAAT AATGGACAGA    1380
TTCAATGGGC AAAAAAAAAA AAAAAAAAAA AAACTCGAG                           1419
```

( 2 ) INFORMATION FOR SEQ ID NO:2:

( i ) SEQUENCE CHARACTERISTICS:
        ( A ) LENGTH: 473 amino acids
        ( B ) TYPE: amino acid
        ( D ) TOPOLOGY: linear ( x i ) SEQUENCE DESCRIPTION: SEQ ID NO:2:

| | | | | | | | | | | | | | | |
|---|---|---|---|---|---|---|---|---|---|---|---|---|---|---|
| Glu 1 | Phe | Gly | Thr | Arg 5 | Ser | Thr | Ser | Met | Glu 10 | Lys | Arg | Lys | Leu 15 | Gln |
| Trp | Arg | Arg | Gly 20 | Arg | Asp | Gly | Ile | Val 25 | Gln | Tyr | Pro | His | Leu 30 | Phe | Phe |
| Ala | Ala | Leu 35 | Ala | Leu | Ala | Leu | Leu 40 | Val | Ala | Asp | Pro | Phe 45 | Gly | Leu | Ser |
| Pro | Leu 50 | Ala | Glu | Val | Asp 55 | Tyr | Arg | Pro | Val | Lys 60 | His | Glu | Leu | Ala | Pro |
| Tyr 65 | Gly | Glu | Val | Met | Gly 70 | Ser | Trp | Pro | Arg | Asp 75 | Asn | Ala | Ser | Arg | Leu 80 |
| Arg | Arg | Gly | Arg | Leu 85 | Glu | Phe | Val | Gly | Glu 90 | Val | Phe | Gly | Pro | Glu 95 | Ser |
| Ile | Glu | Phe | Asp 100 | Leu | Gln | Gly | Arg | Gly 105 | Pro | Tyr | Ala | Gly | Leu 110 | Ala | Asp |
| Gly | Arg | Val 115 | Val | Arg | Trp | Met | Gly 120 | Glu | Glu | Ala | Gly | Trp 125 | Glu | Thr | Phe |
| Ala | Val 130 | Met | Asn | Pro | Asp | Trp 135 | Ser | Glu | Glu | Val | Cys 140 | Ala | Asn | Gly | Val |
| Asn 145 | Ser | Thr | Thr | Arg | Lys 150 | Gln | His | Glu | Lys | Glu 155 | Glu | Phe | Cys | Gly | Arg 160 |
| Pro | Leu | Gly | Leu | Arg 165 | Phe | His | Gly | Glu | Thr 170 | Gly | Glu | Leu | Tyr | Val 175 | Ala |
| Asp | Ala | Tyr | Tyr 180 | Gly | Leu | Met | Val | Val 185 | Gly | Gln | Ser | Gly | Gly 190 | Val | Ala |
| Ser | Ser | Val 195 | Ala | Arg | Glu | Ala | Asp 200 | Gly | Asp | Pro | Ile | Arg 205 | Phe | Ala | Asn |
| Asp | Leu 210 | Asp | Val | His | Arg | Asn 215 | Gly | Ser | Val | Phe | Phe 220 | Thr | Asp | Thr | Ser |
| Met 225 | Arg | Tyr | Ser | Arg | Lys 230 | Asp | His | Leu | Asn | Ile 235 | Leu | Leu | Glu | Gly | Glu 240 |
| Gly | Thr | Gly | Arg | Leu 245 | Leu | Arg | Tyr | Asp | Pro 250 | Glu | Thr | Ser | Ala | Val 255 | His |
| Val | Val | Leu | Lys 260 | Gly | Leu | Val | Phe | Pro 265 | Asn | Gly | Val | Gln | Ile 270 | Ser | Glu |
| Asp | His | Gln 275 | Phe | Leu | Leu | Phe | Ser 280 | Glu | Thr | Thr | Asn | Cys 285 | Arg | Ile | Met |
| Arg | Tyr 290 | Trp | Leu | Glu | Gly | Pro 295 | Arg | Ala | Ser | Glu | Val 300 | Glu | Val | Phe | Ala |
| Asn | Leu 305 | Pro | Gly | Phe | Pro | Asp 310 | Asn | Val | Arg | Ser | Asn 315 | Gly | Arg | Gly | Gln 320 |
| Phe | Trp | Val | Ala | Ile 325 | Asp | Cys | Cys | Arg | Thr 330 | Pro | Ala | Gln | Glu | Val 335 | Phe |
| Ala | Lys | Arg | Pro 340 | Trp | Leu | Arg | Thr | Leu 345 | Tyr | Phe | Lys | Phe | Pro 350 | Leu | Ser |
| Leu | Lys | Val 355 | Leu | Thr | Trp | Lys | Ala 360 | Ala | Arg | Arg | Met | His 365 | Thr | Val | Leu |
| Ala | Leu 370 | Leu | Asp | Gly | Glu | Gly 375 | Arg | Val | Val | Glu | Val 380 | Leu | Glu | Asp | Arg |
| Gly 385 | His | Glu | Val | Met | Lys 390 | Leu | Val | Ser | Glu | Val 395 | Arg | Glu | Val | Gly | Ser 400 |
| Lys | Leu | Trp | Ile | Gly 405 | Thr | Val | Ala | His | Asn 410 | His | Ile | Ala | Thr | Ile 415 | Pro |

```
        Tyr  Pro  Leu  Glu  Asp  Xaa  Pro  Xaa  Ser  Met  Leu  Phe  Gln  Cys  Leu  Leu
                       420                 425                      430

Ile  Cys  Val  Arg  Leu  Xaa  Met  Ser  Asn  Ala  Val  Thr  Gly  Cys  Asn  Leu
                  435                 440                      445

Val  Cys  Val  Trp  Gln  Ile  Gly  Ile  Ile  Met  Asp  Arg  Phe  Asn  Gly  Gln
                  450                 455                      460

Lys  Lys  Lys  Lys  Lys  Lys  Lys  Leu  Glu
        465                      470
```

( 2 ) INFORMATION FOR SEQ ID NO:3:

( i ) SEQUENCE CHARACTERISTICS:
        ( A ) LENGTH: 47 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:3:

```
GCCCTGGCCC  TGGCCCTCCT  AGTCGCGGTC  GCGACCCGTT  CGGCCTC                    47
```

( 2 ) INFORMATION FOR SEQ ID NO:4:

( i ) SEQUENCE CHARACTERISTICS:
        ( A ) LENGTH: 16 amino acids
        ( B ) TYPE: amino acid
        ( D ) TOPOLOGY: linear ( x i ) SEQUENCE DESCRIPTION: SEQ ID NO:4:

```
        Ala  Leu  Ala  Leu  Ala  Leu  Leu  Val  Ala  Val  Ala  Asp  Pro  Phe  Gly  Leu
        1                   5                         10                      15
```

( 2 ) INFORMATION FOR SEQ ID NO:5:

( i ) SEQUENCE CHARACTERISTICS:
        ( A ) LENGTH: 41 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:5:

```
GCCCTGGCCC  TGGCCCTCCT  AGTCGCGACC  CGTTCGGCCT  C                          41
```

( 2 ) INFORMATION FOR SEQ ID NO:6:

( i ) SEQUENCE CHARACTERISTICS:
        ( A ) LENGTH: 14 amino acids
        ( B ) TYPE: amino acid
        ( D ) TOPOLOGY: linear ( x i ) SEQUENCE DESCRIPTION: SEQ ID NO:6:

```
        Ala  Leu  Ala  Leu  Ala  Leu  Leu  Val  Ala  Asp  Pro  Phe  Gly  Leu
        1                   5                         10
```

( 2 ) INFORMATION FOR SEQ ID NO:7:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
GATAGAATTC  GGTACGGGAT  TTTCCCATCC  TACTT                                  35
```

(2) INFORMATION FOR SEQ ID NO:8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:8:

GGTAGAATTC GTTTTCGTTT CCGTCCCGCA AGTT      34

We claim:

1. An isolated nucleotide sequence encoding the amino acid sequence of:

| | | | | | | | | | |
|---|---|---|---|---|---|---|---|---|---|
| Glu | Phe | Gly | Thr | Arg 5 | Ser | Thr | Ser | Met | Glu 10 |
| Lys | Arg | Lys | Leu 15 | Gln | Trp | Arg | Arg | Gly 20 | Arg |
| Asp | Gly | Ile | Val 25 | Gln | Tyr | Pro | His | Leu 30 | Phe |
| Phe | Ala | Ala | Leu 35 | Ala | Leu | Ala | Leu | Leu 40 | Val |
| Ala | Asp | Pro | Phe 45 | Gly | Leu | Ser | Pro | Leu 50 | Ala |
| Glu | Val | Asp | Tyr 55 | Arg | Pro | Val | Lys | His 60 | Glu |
| Leu | Ala | Pro | Tyr 65 | Gly | Glu | Val | Met | Gly 70 | Ser |
| Trp | Pro | Arg | Asp 75 | Asn | Ala | Ser | Arg | Leu 80 | Arg |
| Arg | Gly | Arg | Leu 85 | Glu | Phe | Val | Gly | Glu 90 | Val |
| Phe | Gly | Pro | Glu 95 | Ser | Ile | Glu | Phe | Asp 100 | Leu |
| Gln | Gly | Arg | Gly 105 | Pro | Tyr | Ala | Gly | Leu 110 | Ala |
| Asp | Gly | Arg | Val 115 | Val | Arg | Trp | Met | Gly 120 | Glu |
| Glu | Ala | Gly | Trp 125 | Glu | Thr | Phe | Ala | Val 130 | Met |
| Asn | Pro | Asp | Trp 135 | Ser | Glu | Glu | Val | Cys 140 | Ala |
| Asn | Gly | Val | Asn 145 | Ser | Thr | Thr | Arg | Lys 150 | Gln |
| His | Glu | Lys | Glu 155 | Glu | Phe | Cys | Gly | Arg 160 | Pro |
| Leu | Gly | Leu | Arg 165 | Phe | His | Gly | Glu | Thr 170 | Gly |
| Glu | Leu | Tyr | Val 175 | Ala | Asp | Ala | Tyr | Tyr 180 | Gly |
| Leu | Met | Val | Val 185 | Gly | Gln | Ser | Gly | Gly 190 | Val |
| Ala | Ser | Ser | Val 195 | Ala | Arg | Glu | Ala | Asp 200 | Gly |
| Asp | Pro | Ile | Arg 205 | Phe | Ala | Asn | Asp | Leu 210 | Asp |
| Val | His | Arg | Asn 215 | Gly | Ser | Val | Phe | Phe 220 | Thr |
| Asp | Thr | Ser | Met 225 | Arg | Tyr | Ser | Arg | Lys 230 | Asp |
| His | Leu | Asn | Ile 235 | Leu | Leu | Glu | Gly | Glu 240 | Gly |
| Thr | Gly | Arg | Leu 245 | Leu | Arg | Tyr | Asp | Pro 250 | Glu |
| Thr | Ser | Ala | Val | His 255 | Val | Val | Leu | Lys 260 | Gly |
| Ley | Val | Phe | Pro 265 | Asn | Gly | Val | Gln | Ile 270 | Ser |
| Glu | Asp | His | Gln 275 | Phe | Leu | Leu | Phe | Ser 280 | Glu |
| Thr | Thr | Asn | Cys 285 | Arg | Ile | Met | Arg | Tyr 290 | Trp |
| Leu | Glu | Gly | Pro 295 | Arg | Ala | Ser | Glu | Val 300 | Glu |
| Val | Phe | Ala | Asn | Leu 305 | Pro | Gly | Phe | Pro 310 | Asp |
| Asn | Val | Arg | Ser | Asn 315 | Gly | Arg | Gly | Gln 320 | Phe |
| Trp | Val | Ala | Ile 325 | Asp | Cys | Cys | Arg | Thr 330 | Pro |
| Ala | Gln | Glu | Val 335 | Phe | Ala | Lys | Arg | Pro 340 | Trp |
| Leu | Arg | Thr | Leu 345 | Tyr | Phy | Lys | Phe | Pro 350 | Leu |
| Ser | Leu | Lys | Val 355 | Leu | Thr | Trp | Lys | Ala 360 | Ala |
| Arg | Arg | Met | His 365 | Thr | Val | Leu | Ala | Leu 370 | Leu |
| Asp | Gly | Glu | Gly | Arg 375 | Val | Val | Glu | Val 380 | Leu |
| Glu | Asp | Arg | Gly 385 | His | Glu | Val | Met | Lys 390 | Leu |
| Val | Ser | Glu | Val 395 | Arg | Glu | Val | Gly | Ser 400 | Lys |
| Leu | Trp | Ile | Gly 405 | Thr | Val | Ala | His | Asn 410 | His |
| Ile | Ala | Thr | Ile 415 | Pro | Tyr | Pro | Leu | Glu 420 | Asp |
| Xaa | Pro | Xaa | Ser 425 | Met | Leu | Phe | Gln | Cys 430 | Leu |
| Leu | Ile | Cys | Val 435 | Arg | Leu | Xaa | Met | Ser 440 | Asn |
| Ala | Val | Thr | Gly 445 | Cys | Asn | Leu | Val | Cys 450 | Val |
| Trp | Gln | Ile | Gly 455 | Ile | Ile | Met | Asp | Arg 460 | Phe |
| Asn | Gly | Gln | Lys 465 | Lys | Lys | Lys | Lys 470 | Lys | Leu | Glu |

2. An RNA molecue according to claim 1.
3. A DNA molecule according to claim 1.
4. An isolated DNA molecule that mediates male fertility in maize comprising:

| | | | |
|---|---|---|---|
| GAATTCGGCA | CGAGGTCCAC | CAGCATGGAG | |
| GAGAAGAGGA | AGCTGCAGTG | 50 | |
| GCGGCGAGGG | CGTGATGGCA | TCGTGCAGTA | |
| CCCTCACCTG | TTCTTCGCGG | 100 | |
| CCCTGGCCCT | GGCCCTCCTA | GTCGCGGACC | |
| CGTTCGGCCT | CAGTCCGCTG | 150 | |
| GCCGAGGTCG | ACTACCGGCC | GGTGAAGCAC | |
| GAGCTCGCGC | CGTACGGGGA | 200 | |
| GGTCATGGGC | AGCTGGCCCA | GAGACAATGC | |
| CAGCCGGCTC | AGGCGCGGGA | 250 | |
| GGCTGGAGTT | CGTCGGCGAG | GTGTTCGGGC | |
| CGGAGTCCAT | CGAGTTCGAT | 300 | |
| CTCCAGGGCC | GCGGGCCGTA | CGCCGGCCTC | |
| GCCGACGGCC | GCGTCGTGCG | 350 | |
| GTGGATGGGC | GAGGAGGCCG | GGTGGGAGAC | |
| GTTCGCCGTC | ATGAATCCTG | 400 | |
| ACTGGTCAGA | AGAAGTCTGT | GCCAATGGAG | |
| TGAACTCAAC | GACGAGGAAG | 450 | |
| CAGCACGAGA | AGGAGGAGTT | CTGCGGCCGG | |
| CCGCTCGGCC | TGAGGTTCCA | 500 | |
| CGGGGAGACC | GGCGAGCTCT | ACGTCGCCGA | |
| CGCGTACTAC | GGTCTCATGG | 550 | |
| TCGTTGGCCA | GAGCGGCGGC | GTGGCGTCCT | |
| CCGTCGCGAG | GGAAGCCGAC | 600 | |
| GGGGACCCCA | TCCGGTTCGC | GAACGACCTC | |
| GATGTGCACA | GGAATGGATC | 650 | |
| CGTATTCTTC | ACTGACACGA | GCATGAGATA | |
| CAGCAGAAAG | GACCATCTGA | 700 | |
| ACATCCTGTT | AGAAGGAGAA | GGCACCGGGA | |
| GGCTGCTCAG | GTACGATCCA | 750 | |
| GAAACAAGTG | CTGTCCATGT | CGTGCTCAAG | |
| GGACTGGTGT | TCCCAAACGG | 800 | |
| CGTGCAGATC | TCAGAAGACC | ATCAGTTTCT | |
| TCTCTTCTCC | GAGACAACAA | 850 | |
| ACTGCAGGAT | AATGAGGTAC | TGGCTGGAAG | |
| GCCCAAGAGC | GAGCGAGGTA | 900 | |
| GAGGTGTTCG | CGAACCTGCC | GGGCTTCCCC | |
| GACAACGTGC | GCTCCAACGG | 950 | |
| CAGGGGCCAG | TTCTGGGTGG | CGATCGACTG | |
| CTGCCGGACG | CCAGCGCAGG | 1000 | |
| AGGTGTTCGC | CAAGAGGCCG | TGGCTCCGGA | |
| CCCTGTACTT | CAAGTTCCCG | 1050 | |
| CTGTCGCTCA | AGGTGCTCAC | TTGGAAGGCC | |
| GCCAGGAGGA | TGCACACGGT | 1100 | |
| GCTCGCGCTC | CTCGACGGCG | AAGGGCGCGT | |
| CGTGGAGGTG | CTCGAGGACC | 1150 | |
| GGGGCCACGA | GGTGATGAAG | CTGGTGAGCG | |
| AGGTGCGGGA | GGTGGGCAGC | 1200 | |
| AAGCTGTGGA | TCGGAACCGT | GGCGCACAAC | |
| CACATCGCCA | CCATCCCCTA | 1250 | |
| CCCTTTAGAG | GACTAACCAT | GATCTATGCT | |
| GTTTCAATGC | CTCCTAATCT | 1300 | |
| GTGTACGTCT | ATAAATGTCT | AATGCAGTCA | |

```
                              -continued
CTGGTTGTAA      TCTTGTTTGT         1350

TTCAATGGGC      AAAAAAAAAA         1400

AAAAAAAAAA      AAACTCGAG          1419
```

5. A plasmid vector containing the nucleotide sequence of claim 1.

6. A method for mediating male fertility in maize comprising repressing expression of a nucleotide sequence encoding the amino acid sequence:

| Arg | Ile | Met | Arg | Tyr | Trp | Leu | Glu | Gly | Pro | Arg |
|---|---|---|---|---|---|---|---|---|---|---|
|  |  |  |  | 290 |  |  |  |  | 295 |  |
| Ala | Ser | Glu | Val | Glu | Val | Phe | Ala | Asn | Leu | Pro |
|  |  |  | 300 |  |  |  |  | 305 |  |  |
| Gly | Phr | Pro | Asp | Asn | Val | Arg | Ser | Asn | Gly | Arg |
|  |  | 310 |  |  |  |  | 315 |  |  |  |
| Gly | Gln | Phe | trp | Val | Ala | Ile | Asp | Cys | Cys | Arg |
|  | 320 |  |  |  |  | 325 |  |  |  |  |
| Thr | Pro | Ala | Gln | Glu | Val | Phe | Ala | Lys | Arg | Pro |
| 330 |  |  |  |  | 335 |  |  |  |  | 340 |
| Trp | Leu | Arg | Thr | Leu | Tyr | Phe | Lys | Phe | Pro | Leu |
|  |  |  |  | 345 |  |  |  |  | 350 |  |
| Ser | Leu | Lys | Val | Leu | Thr | Trp | Lys | Ala | Ala | Arg |
|  |  |  |  | 355 |  |  |  | 360 |  |  |
| Arg | Met | His | Thr | Val | Leu | Ala | Leu | Leu | Asp | Gly |
|  |  | 365 |  |  |  |  | 370 |  |  |  |
| Glu | Gly | Arg | Val | Val | Glu | Val | Leu | Glu | Asp | Arg |
|  | 375 |  |  |  |  | 380 |  |  |  |  |
| Gly | His | Glu | Val | Met | Lys | Leu | Val | Ser | Glu | Val |
| 385 |  |  |  |  | 390 |  |  |  |  | 395 |
| Arg | Glu | Val | Gly | Ser | Lys | Leu | Trp | Ile | Gly | Thr |
|  |  |  |  | 400 |  |  |  |  | 405 |  |
| Val | Ala | His | Asn | His | Ile | Ala | Thr | Ile | Pro | Tyr |
|  |  |  | 410 |  |  |  |  | 415 |  |  |
| Pro | Leu | Glu | Asp | Xaa | Pro | Xaa | Ser | Met | Leu | Phe |
|  |  |  | 420 |  |  |  | 425 |  |  |  |
| Gln | Cys | Leu | Leu | Ile | Cys | Val | Arg | Leu | Xaa | Met |
|  | 430 |  |  |  |  | 435 |  |  |  |  |
| Ser | Asn | Ala | Val | Thr | Gly | Cys | Asn | Leu | Val | Cys |
| 440 |  |  |  |  | 445 |  |  |  |  | 450 |
| Val | Trp | Gln | Ile | Gly | Ile | Ile | Met | Asp | Arg | Phe |
|  |  |  |  | 455 |  |  |  |  | 460 |  |
| Asn | Gly | Gln | Lys | Lys | Lys | Lys | Lys | Lys | Lys | Leu |
|  |  |  | 465 |  |  |  |  | 470 |  |  |
| Glu |  |  |  | 475 |  |  |  |  |  |  |

7. A method for mediating male fertility in maizes comprising repressing expression of a DNA molecule comprising the sequence:

| Glu | Phe | Gly | Thr | Arg | Ser | Thr | Ser | Met | Glu | Glu | Lys | Arg | Lys | Leu |
|---|---|---|---|---|---|---|---|---|---|---|---|---|---|---|
|  |  |  |  | 5 |  |  |  |  | 10 |  |  |  |  | 15 |
| Gln | Trp | Arg | Arg | Gly | Arg | Asp | Gly | Ile | Val | Gln | Tyr | Pro | His | Leu |
|  |  |  |  | 20 |  |  |  |  | 25 |  |  |  |  | 30 |
| Phe | Phe | Ala | Ala | Leu | Ala | Leu | Ala | Leu | Leu | Val | Ala | Asp | Pro | Phe |
|  |  |  |  | 35 |  |  |  |  | 40 |  |  |  |  | 45 |
| Gly | Leu | Ser | Pro | Leu | Ala | Glu | Val | Asp | Tyr | Arg | Pro | Val | Lys | His |
|  |  |  |  | 50 |  |  |  |  | 55 |  |  |  |  | 60 |
| Glu | Leu | Ala | Pro | Tyr | Gly | Glu | Val | Met | Gly | Ser | Trp | Pro | Arg | Asp |
|  |  |  |  | 65 |  |  |  |  | 70 |  |  |  |  | 75 |
| Asn | Ala | Ser | Arg | Leu | Arg | Arg | Gly | Arg | Leu | Glu | Phe | Val | Gly | Glu |
|  |  |  |  | 80 |  |  |  |  | 85 |  |  |  |  | 90 |
| Val | Phe | Gly | Pro | Glu | Ser | Ile | Glu | Phe | Asp | Leu | Gln | Gly | Arg | Gly |
|  |  |  |  | 95 |  |  |  |  | 100 |  |  |  |  | 105 |
| Pro | Tyr | Ala | Gly | Leu | Ala | Asp | Gly | Arg | Val | Val | Arg | Trp | Met | Gly |
|  |  |  |  | 110 |  |  |  |  | 115 |  |  |  |  | 120 |
| Glu | Glu | Ala | Gly | Trp | Glu | Thr | Phe | Ala | Val | Met | Asn | Pro | Asp | Trp |
|  |  |  |  | 125 |  |  |  |  | 130 |  |  |  |  | 135 |
| Ser | Glu | Glu | Val | Cys | Ala | Asn | Gly | Val | Asn | Ser | Thr | Thr | Arg | Lys |
|  |  |  |  | 140 |  |  |  |  | 145 |  |  |  |  | 150 |
| Gln | His | Glu | Lys | Glu | Glu | Phe | Cys | Gly | Arg | Pro | Leu | Gly | Leu | Arg |
|  |  |  |  | 155 |  |  |  |  | 160 |  |  |  |  | 165 |
| Phe | His | Gly | Glu | Thr | Gly | Glu | Leu | Tyr | Val | Ala | Asp | Ala | Tyr | Tyr |
|  |  |  |  | 170 |  |  |  |  | 175 |  |  |  |  | 180 |
| Gly | Leu | Met | Val | Val | Gly | Gln | Ser | Bly | Gly | Val | Ala | Ser | Ser | Val |
|  |  |  |  | 185 |  |  |  |  | 190 |  |  |  |  | 195 |

| | | | | | | | | | | | | | |
|---|---|---|---|---|---|---|---|---|---|---|---|---|---|
|Ala|Arg|Glu|Ala|Asp|Gly|Asp|Pro|Ile|Arg|Phe|Ala|Asn|Asp|Leu|
| | | | |200| | | |205| | | | |210|
|Asp|Val|His|Arg|Asn|Gly|Ser|Val|Phe|Phe|Thr|Asp|Thr|Ser|Met|
| | | | |215| | | |220| | | | |225|
|Arg|Tyr|Ser|Arg|Lys|Asp|His|Leu|Asn|Ile|Leu|Leu|Glu|Gly|Glu|
| | | | |230| | | |235| | | | |240|
|Gly|Thr|Gly|Arg|Leu|Leu|Arg|Tyr|Asp|Pro|Glu|Thr|Ser|Ala|Val|
| | | | |245| | | |250| | | | |255|
|His|Val|Val|Leu|Lys|Gly|Leu|Val|Phe|Pro|Asn|Gly|Val|Gln|Ile|
| | | | |260| | | |265| | | | |270|
|Ser|Glu|Asp|His|Gln|Phe|Leu|Leu|Phe|Ser|Glu|Thr|Thr|Asn|Cys|
| | | | |275| | | |280| | | | |285|

```
GAATTCGGCA   CGAGGTCCAC   CAGCATGGAG   GAGAAGAGGA   AGCTGCAGTG    50

GCGGCGAGGG   CGTGATGGCA   TCGTGCAGTA   CCCTCACCTG   TTCTTCGCGG   100

CCCTGGCCCT   GGCCCTCCTA   GTCGCGGACC   CGTTCGGCCT   CAGTCCGCTG   150

GCCGAGGTCG   ACTACCGGCC   GGTGAAGCAC   GAGCTCGCGC   CGTACGGGGA   200

GGTCATGGGC   AGCTGGCCCA   GAGACAATGC   CAGCCGGCTC   AGGCGCGGGA   250

GGCTGGAGTT   CGTCGGCGAG   GTGTTCGGGC   CGGAGTGCAT   CGAGTTCGAT   300

CTCCAGGGCC   GCGGGCCGTA   CGCCGGCCTC   GCCGACGGCC   GCGTCGTGCG   350

GTGGATGGGC   GAGGAGGCCG   GGTGGAGAC    GTTCGCCGTC   ATGAATCCTG   400

ACTGGTCAGA   AGAAGTCTGT   GCCAATGGAG   TGAACTCAAC   GACGAGGAAG   450

CAGCACGAGA   AGGAGGAGTT   CTGCGGCCGG   CCGCTCGGCC   TGAGGTTCCA   500

CGGGGAGACC   GGCGAGCTCT   ACGTCGCCGA   CGCGTACTAC   GGTCTCATGG   550

TCGTTGGCCA   GAGCGGCGGC   GTGGCGTCCT   CCGTCGCGAG   GGAAGCCGAC   600

GGGGACCCCA   TCCGGTTCGC   GAACGACCTC   GATGTGCACA   GGAATGGATC   650

CGTATTCTTC   ACTGACACGA   GCATGAGATA   CAGCAGAAAG   GACCATCTGA   700

ACATCCTGTT   AGAAGGAGAA   GGCACCGGGA   GGCTGCTCAG   GTACGATCCA   750

GAAACAAGTG   CTGTCCATGT   CGTGCTCAAG   GGACTGGTGT   TCCCAAACGG   800

CGTGCAGATC   TCAGAAGACC   ATCAGTTTCT   TCTCTTCTCC   GAGACAACAA   850

ACTGCAGGAT   AATGAGGTAC   TGGCTGGAAG   GCCCAAGAGC   GAGCGAGGTA   900

GAGGTGTTCG   CGAACCTGCC   GGGCTTCCCC   GACAACGTGC   GCTCCAACGG   950

CAGGGGCCAG   TTCTGGGTGG   CGATCGACTG   CTGCCGGACG   CCAGCGCAGG  1000

AGGTGTTCGC   CAAGAGGCCG   TGGCTCCGGA   CCCTGTACTT   CAAGTTCCCG  1050
```

-continued

| | | | | | |
|---|---|---|---|---|---|
| CTGTCGCTCA | AGGTGCTCAC | TTGGAAGGCC | GCCAGGAGGA | TGCACACGGT | 1100 |
| GCTCGCGCTC | CTCGACGGCG | AAGGGCGCGT | CGTGGAGGTG | CTCGAGGACC | 1150 |
| GGGGCCACGA | GGTGATGAAG | CTGGTGAGCG | AGGTGCGGGA | GGTGGGCAGC | 1200 |
| AAGCTGTGGA | TCGGAACCGT | GGCGCACAAC | CACATCGCCA | CCATCCCCTA | 1250 |
| CCCTTTAGAG | GACTAACCAT | GATCTATGCT | GTTTCAATGC | CTCCTAATCT | 1300 |
| GTGTACGTCT | ATAAATGTCT | AATGCAGTCA | CTGGTTGTAA | TCTTGTTTGT | 1350 |
| GTTTGGCAAA | TTGGCATAAT | AATGGACAGA | TTCAATGGGC | AAAAAAAAAA | 1400 |
| AAAAAAAAAA | AAACTCGAG | | | | 1419 |

8. The method of claim 6 wherein expression is repressed by mutation of said nucleotide sequence.

9. The method of claim 6 wherein expression is repressed by delivering into said maize a second nucleotide sequence which operates to repress expression of the first nucleotide sequence.

10. The method of claim 7 wherein expression is repressed by mutation of said DNA molecule.

11. The method of claim 7 wherein expression is repressed by delivering into said maize a nucleotide sequence molecule oriented in the antisense direction relative to said DNA molecule thereby repressing expression of said DNA molecule.

12. The method of claim 7 wherein expression is repressed by delivering into said maize a nucleotide sequence which operates to repress expression of said DNA molecule.

13. A method of providing heritable externally controllable male sterility in maize comprising:
linking the DNA molecule of claim 3 in an expression sequence with an inducible promoter responsive to external control;
delivering the expression sequence into the genome of the maize; and
inactivating the DNA molecule which codes for the product of the DNA molecule of claim 3 from the native genome of the maize.

14. A method of providing heritable externally controllable male sterility in maize comprising:
linking the DNA molecule of claim 4 in an expression sequence with an inducible promoter responsive to external control
delivering the expression sequence into the genome of the maize plant; and
inactivating the DNA molecule which codes for the product of the DNA molecule of claim 4 from the native genome of the maize.

15. A method of reproducing a maize plant and seed having heritable, externally controllable male sterility comprising: replacing a first native DNA molecule in the plant which codes for the product of the DNA molecule of claim 3 with a second DNA molecule of claim 3 which is linked in an expression sequence with an inducible promoter;
planting seed of the plant to provide growing male sterile plants;
inducing conversion of the growing plants to male fertile form under conditions which induce the promoter to express the second DNA molecule; and
open-pollinating the growing plants in isolation to produce seed; and harvesting the seed.

16. A method of reproducing a maize plant and seed having heritable, externally controllable male sterility comprising: replacing a first native DNA molecule in the plant which codes for the product of the DNA molecule of claim 4 with a second DNA molecule of claim 4 which is linked in an expression sequence with an inducible promoter;
planting seed of the plant to provide growing male sterile plants;
inducing conversion of the growing plants to male fertile form under conditions which induce the promoter to express the second DNA molecule; and
open-pollinating the growing plants in isolation to produce seed; and harvesting the seed.

17. A method of producing maize hybrid seed, comprising the steps of:
planting in cross-pollinating juxtaposition, a first seed from a selected male fertile parent line and a second seed selected from a female parent line having male sterility resulting from the replacement of a first native DNA molecule which encodes for the amino acid sequence set forth in claim 3 with a second DNA molecule of claim 3 linked in an expression sequence with an inducible promoter responsive to external control;
growing the seed to mature plants under conditions which do not induce expression of the second DNA molecule;
cross-pollinating the male sterile female plant with pollen from the male fertile plant; and
harvesting seed from the male sterile female plant.

18. An expression cassette containing the nucleotide sequence of claim 1 operably linked to regulatory sequences which cause the expression of the nucleotide sequences in plant cells.

* * * * *